United States Patent [19]

Suchy et al.

[11] Patent Number: 5,232,898
[45] Date of Patent: Aug. 3, 1993

[54] HETEROCYCLIC SUBSTITUTED URACIL DERIVATIVES

[75] Inventors: Milos Suchy, Kaiseraugst; Paul Winternitz, Greifensee; Martin Zeller, Baden, all of Switzerland

[73] Assignee: Ciba-Geigy Corporation, Ardsley, N.Y.

[21] Appl. No.: 807,024

[22] Filed: Dec. 9, 1991

Related U.S. Application Data

[63] Continuation-in-part of Ser. No. 634,216, Feb. 8, 1991, abandoned.

[30] Foreign Application Priority Data

Jun. 9, 1989 [CH] Switzerland ............... 2166/89

[51] Int. Cl.[5] .................. A01N 43/76; A01N 43/78; C07D 413/02; C07D 417/02
[52] U.S. Cl. .................. 504/243; 544/52; 544/105; 544/310; 544/312
[58] Field of Search .................. 544/311, 312, 310; 71/90, 92; 504/243

[56]  References Cited

U.S. PATENT DOCUMENTS

| | | | |
|---|---|---|---|
| 4,761,174 | 8/1988 | Chang et al. | 71/92 |
| 4,981,508 | 1/1991 | Strunk et al. | 71/92 |
| 5,084,084 | 1/1992 | Satow et al. | 71/92 |

FOREIGN PATENT DOCUMENTS 0408382  1/1991  European Pat. Off.

*Primary Examiner*—Mukund J. Shah
*Assistant Examiner*—Philip I. Datlow
*Attorney, Agent, or Firm*—Wenderoth, Lind & Ponack

[57]  ABSTRACT

The invention is concerned with compounds of the formula

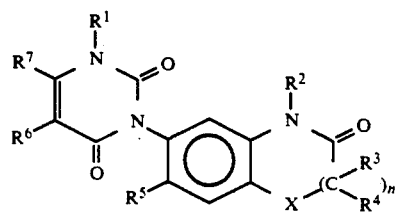

I wherein $R^1$, $R^2$, $R^3$, $R^4$, $R^5$, $R^6$, $R^7$, n and X have the significances given in the description, as well as enol ethers and salts thereof and their manufacture. The compounds have herbicidal properties and are accordingly suitable as active ingredients of weed control compositions. The invention is also concerned with weed control compositions containing one or more of such substances as well as the use of the substances or compositions for the control of weeds. Certain starting materials, which also have herbicidal activity, and their production are also described.

14 Claims, No Drawings

HETEROCYCLIC SUBSTITUTED URACIL DERIVATIVES

This application is a continuation-in-part of application Ser. No. 07/634,216 filed Feb. 8, 1991, now abandoned.

The present invention is concerned with heterocyclic compounds, namely 3-aryluracils of the general formula

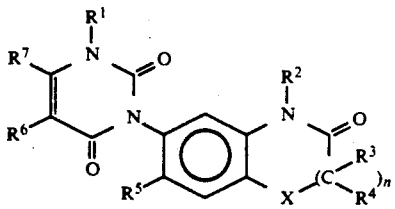

wherein
$R^1$ signifies hydrogen, $C_{1-4}$-alkyl, $C_{1-4}$-haloalkyl, $C_{2-5}$-alkenyl or $C_{3-5}$-alkynyl,
$R^2$ signifies hydrogen, $C_{1-4}$-alkyl, $C_{1-4}$-haloalkyl, $C_{1-4}$-alkoxy-$C_{1-4}$-alkyl, $C_{1-4}$-alkoxy-$C_{1-4}$-alkoxy-$C_{1-4}$-alkyl, $C_{2-5}$-cyanoalkyl, $C_{2-5}$-carboxyalkyl, $C_{2-5}$-alkoxycarbonyl-$C_{1-4}$-alkyl, $C_{2-5}$-haloalkoxycarbonyl-$C_{1-4}$-alkyl, $C_{1-4}$-alkoxy-$C_{2-5}$-alkoxycarbonyl-$C_{1-4}$-alkyl, $C_{2-5}$-alkoxycarbonyl-$C_{2-5}$-alkoxycarbonyl-$C_{1-4}$-alkyl, $C_{4-7}$-cycloalkyloxycarbonyl-$C_{1-4}$-alkyl, carbamoyl-$C_{1-4}$-alkyl, mono($C_{1-4}$-alkyl)carbamoyl-$C_{1-4}$-alkyl, di($C_{1-4}$-alkyl)carbamoyl-$C_{1-4}$-alkyl, $C_{3\ or\ 4}$-alkenyl, $C_{3\ or\ 4}$-haloalkenyl, cinnamyl, $C_{3\ or\ 4}$-alkynyl or $C_{3\ or\ 4}$-haloalkynyl,
$R^3$ and $R^4$ each independently signify hydrogen, halogen, $C_{1-4}$-alkyl or phenyl,
$R^5$ signifies hydrogen, fluorine or chlorine,
$R^6$ signifies hydrogen, halogen or $C_{1-4}$-alkyl,
$R^7$ signifies $C_{1-4}$-alkyl or, where $R^1$ is not $C_{1-4}$-haloalkyl, also $C_{1-4}$-haloalkyl,
n signifies zero or 1
and
X signifies oxygen or sulphur,
and the enol ethers of those compounds of formula I in which $R^1$ signifies $C_{1-4}$-alkyl, $C_{2-5}$-alkenyl or $C_{3-5}$-alkynyl as well as salts of those compounds of formula I in which $R^1$ signifies hydrogen, $R^2$ signifies hydrogen and/or $R^2$ signifies $C_{2-5}$-carboxyalkyl,
with the proviso that n signifies zero if $R^7$ is $C_{1-4}$fluoroalkyl and $R^6$ is hydrogen or halogen.

The above-mentioned enol ethers are thus the compounds of the formula

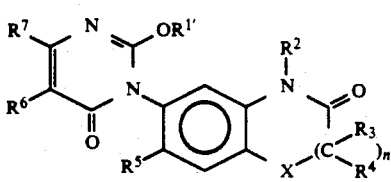

wherein $R^2$, $R^3$, $R^4$, $R^5$, $R^6$, $R^7$, n and X have the significances given above and $R^{1'}$ signifies $C_{1-4}$-alkyl, $C_{2-5}$-alkenyl or $C_{3-5}$-alkynyl.

The compounds in accordance with the invention, namely the compounds of formula I and their enol ethers and salts, have herbicidal activity and are suitable as active ingredients of weed control compositions. Accordingly, the invention also embraces weed control compositions which contain compounds in accordance with the invention as active ingredients, a process for the manufacture of these compounds as well as the use of the compounds or compositions for the control of weeds.

In formula I above "halogen" embraces fluorine, chlorine, bromine or iodine. The alkyl, alkenyl and alkynyl residues can be straight-chain or branched, and this also applies to the or each alkyl, alkenyl or alkynyl part of larger groups such as alkoxyalkoxyalkyl. A haloalkyl, haloalkenyl or haloalkynyl group can have one or more (similar or different) halogen atoms, and this also applies to haloalkyl as part of a larger group such as haloalkoxycarbonylalkyl. Depending on the number of carbon atoms therein, the alkenyl and alkynyl residues can have more than one double bond and triple bond, respectively.

The salts of the compounds of formula I are especially alkali metal salts, e.g. sodium and potassium salts; alkaline earth metal salts, e.g. calcium and magnesium salts; ammonium salts, i.e. unsubstituted ammonium salts and mono- or multiply-substituted ammonium salts, e.g. triethylammonium and methylammonium salts, as well as salts with other organic bases, e.g. with pyridine.

The presence of at least one asymmetric carbon atom in the compounds I and in their enol ethers Ia means that the compounds can occur in optically isomeric forms. Geometric isomerism can also occur when an aliphatic C=C or C=N double bond is present. Moreover, keto-enol tautomerism [—NH—CO—→—N=C(OH)-] can occur in those compounds of formula I in which $R^1$ signifies hydrogen. Formula I is intended to embrace all of these possible isomeric forms as well as mixtures thereof.

An interesting group of compounds in accordance with the invention comprises those compounds of formula I in which $R^1$ signifies hydrogen or $C_{1-4}$-alkyl, $R^2$ signifies hydrogen, $C_{1-4}$-alkyl, $C_{1-4}$-haloalkyl, $C_{1-4}$-alkoxy-$C_{1-4}$-alkyl, $C_{2-5}$-cyanoalkyl, $C_{2-5}$-alkoxycarbonyl-$C_{1-4}$-alkyl, carbamoyl-$C_{1-4}$-alkyl, di($C_{1-4}$-alkyl)carbamoyl-$C_{1-4}$-alkyl, $C_{3\ or\ 4}$-alkenyl, cinnamyl or $C_{3\ or\ 4}$-alkynyl, $R^3$ and $R^4$ each independently signify hydrogen or $C_{1-4}$-alkyl, $R^5$ signifies hydrogen or fluorine, $R^6$ signifies hydrogen or halogen, $R^7$ signifies $C_{1-4}$-alkyl or $C_{1-4}$-haloalkyl, n signifies zero or 1 and X signifies oxygen or sulphur, as well as the enol ethers of those compounds of formula I in which $R^1$ signifies $C_{1-4}$-alkyl.

Independently of each other $R^1$ preferably signifies straight-chain $C_{1-4}$-alkyl, especially methyl, or $C_{1-4}$-haloalkyl, especially difluoromethyl; $R^2$ preferably signifies $C_{1-4}$-alkyl, $C_{1-4}$-alkoxy-$C_{1-4}$-alkyl, $C_{3\ or\ 4}$-alkenyl, $C_{3\ or\ 4}$-alkynyl, $C_{1-4}$-haloalkyl, $C_{3\ or\ 4}$-haloalkenyl or $C_{3\ or\ 4}$-haloalkynyl, especially the first, second, third or fourth of such groups; $R^3$ and $R^4$ each preferably signify hydrogen or $C_{1-4}$-alkyl, especially hydrogen; $R^5$ preferably signifies hydrogen or fluorine; $R^6$ preferably signifies hydrogen, fluorine, chlorine, bromine or methyl, especially hydrogen; $R^7$ preferably signifies $C_{1-4}$-alkyl, especially $C_{1-3}$-alkyl such as methyl or ethyl, or $C_{1-4}$-fluoroalkyl, especially trifluoromethyl or pentafluoroethyl; and n preferably signifies zero when X signifies sulphur or n preferably signifies 1 when X signifies oxygen.

Preferred individual compounds of formula I are:

6-Ethyl-3-[4-allyl-3,4-dihydro-7-fluoro-3-oxo-2H-1,4-benzoxazin-6-yl]-5-bromo-1-methyl-2,4(1H,3H)-pyrimidinedione.

3-[3,4-dihydro-7-fluoro-3-oxo-4-(2-propynyl)-2H-1,4-benzoxazin-6-yl]-1-methyl-6-(n-propyl)-2,4(1H,3H)-pyrimidinedione, 6-ethyl-3-[3,4-dihydro-7-fluoro-4-isopropyl-3-oxo-2H-1,4-benzoxazin-6-yl]-1-methyl-2,4(1H,3H)-pyrimidinedione, 6-ethyl-3-[4-sec.butyl-3,4-dihydro-7-fluoro-3-oxo-2H-1,4-benzoxazin-6-yl]-1-methyl-2,4(1H,3H)-pyrimidinedione, 6-ethyl-3-[3,4-dihydro-7-fluoro-4-(1-methoxyethyl)-3-oxo-2H-1,4-benzoxazin-6-yl]-1-methyl-2,4(1H,3H)-pyrimidinedione, 6-ethyl-3-[3,4-dihydro-7-fluoro-4-(1-methoxypropyl)-3-oxo-2H-1,4-benzoxazin-6-yl]-1-methyl-2,4(1H,3H)-pyrimidinedione, 6-ethyl-3-[4-allyl-3,4-dihydro-7-fluoro-3-oxo-2H-1,4-benzoxazin-6-yl]-1-methyl-2,4(1H,3H)-pyrimidinedione, 6-ethyl-3-[3,4-dihydro-7-fluoro-4-(1-methyl-2-propenyl)-3-oxo-2H-1,4-benzoxazin-6yl]-1-methyl-2,4(1H,3H)-pyrimidinedione, 6-ethyl-3-[3,4-dihydro-7-fluoro-3-oxo-4-(2-propynyl)-2H-1,4-benzoxazin-6-yl]-1-methyl-2,4(1H,3H)-pyrimidinedione, 6-ethyl-3-[3,4-dihydro-7-fluoro-4-(1-methyl-2-propynyl)-3-oxo-2H-1,4-benzoxazin-6-yl]-1-methyl-2,4-(1H,3H)-pyrimidinedione, 6-ethyl-3-[6-fluoro-3-isopropyl-2-oxo-5-benzothiazolinyl]-1-methyl-2,4(1H,3H)-pyrimidinedione, 6-ethyl-3-[3-sec.butyl-6-fluoro-2-oxo-5-benzothiazolinyl]-1-methyl-2,4(1H,3H)-pyrimidinedione, 6-ethyl-3-[6-fluoro-3-(1-methoxyethyl)-2-oxo-5-benzothiazolinyl]-1-methyl-2,4(1H,3H)-pyrimidinedione, 6-ethyl-3-[6-fluoro-3-(1-methoxypropyl)-2-oxo-5-benzothiazolinyl]-1-methyl-2,4(1H,3H)-pyrimidinedione, 6-ethyl-3-[3-allyl-6-fluoro-2-oxo-5-benzothiazolinyl]-1-methyl-2,4(1H,3H)-pyrimidinedione, 6-ethyl-3-[6-fluoro-3-(1-methyl-2-propenyl)-2-oxo-5-benzothiazolinyl]-1-methyl-2,4(1H,3H)-pyrimidinedione, 6-ethyl-3-[6-fluoro-2-oxo-3-(2-propinyl)-5-benzothiazolinyl]-1-methyl-2,4(1H,3H)-pyrimidinedione and 6-ethyl-3-[6-fluoro-3-(1-methyl-2-propinyl)-2-oxo-5-benzothiazolinyl]-1-methyl-2,4(1H,3H)-pyrimidinedione.

Representatives of compounds of formula I are:

Those compounds I in which $R^1$ and $R^7$ each signify methyl, $R^3$, $R^4$ and $R^6$ each signify hydrogen, $R^5$ signifies fluorine, n signifies 1, X signifies oxygen and $R^2$ signifies ethyl, n-propyl, 2-fluoroethyl, methoxymethyl, 2-methoxyethyl, methoxycarbonylmethyl, 1-methoxycarbonyl-ethyl, 2-methoxycarbonyl-ethyl, cyclopentyloxycarbonylmethyl, carbamoylmethyl, dimethylcarbamoylmethyl, 3,3-dichloro-2-propenyl, cinnamyl or 3-chloro-2-propynyl, 3-[3,4-dihydro-7-fluoro-3-oxo-4-(2-propynyl)-2H-1,4-benzoxazin-6-yl]-1,5,6-trimethyl-2,4(1H,3H)-pyrimidinedione, 3-[3,4-dihydro-2,2-dimethyl-7-fluoro-3-oxo-4-(2-propynyl)-2H-1,4-benzoxazin-6-yl]-1,6-dimethyl-2,4(1H,3H)-pyrimidinedione, 3-[2-ethyl-3,4-dihydro-7-fluoro-3-oxo-4-(2-propynyl)-2H-1,4-benzoxazin-6-yl]-1,6-dimethyl-2,4(1H,3H)-pyrimidinedione, 3-[3,4-dihydro-3-oxo-4-(2-propynyl)-2H-1,4-benzoxazin-6-yl]-1,6-dimethyl-2,4(1H,3H)-pyrimidinedione, 3-[7-chloro-3,4-dihydro-3-oxo-4-(2-propynyl)-2H-1,4-benzoxazin-6-yl]-1,6-dimethyl-2,4(1H,3H)-pyrimidinedione, those compounds I in which $R^1$ signifies difluoromethyl, $R^3$, $R^4$ and $R^6$ each signify hydrogen, $R^5$ signifies fluorine, $R^7$ signifies methyl, n signifies 1, X signifies oxygen and $R^2$ signifies ethyl, n-propyl, allyl or propargyl, 6-ethyl-1-difluoromethyl-3-[3,4-dihydro-7-fluoro-3-oxo-4-(2-propynyl)-2H-1,4-benzoxazin-6-yl]-2,4(1H,3H)-pyrimidinedione, 1-difluoromethyl-3-[3,4-dihydro-7-fluoro-2-methyl-3-oxo-4-(2-propynyl)-2H-1,4-benzoxazin-6-yl]-6-methyl-2,4(1H,3H)-pyrimidinedione, those compounds I in which $R^1$ signifies methyl, $R^3$, $R^4$, $R^5$ and $R^6$ each signify hydrogen, $R^7$ signifies trifluoromethyl, n signifies 1, X signifies oxygen and $R^2$ signifies ethyl, n-propyl, 2-fluoroethyl, methoxymethyl, 2-methoxyethyl, cyanomethyl, methoxycarbonylmethyl, 1-methoxycarbonyl-ethyl, 2-methoxycarbonyl-ethyl, cyclopentyloxycarbonylmethyl, carbamoylmethyl, dimethylcarbamoylmethyl, allyl, 3,3-dichloro-2-propenyl, cinnamyl, 1-methyl-2-propynyl or 3-chloro-2-propynyl, 3-[3,4-dihydro-2-methyl-3-oxo-4-(2-propynyl)-2H-1,4-benzoxazin-6-yl]-1-methyl-6-trifluoromethyl-2,4-(1H,3H)-pyrimidinedione, 3-[7-chloro-3,4-dihydro-3-oxo-4-(2-propynyl)-2H-1,4-benzoxazin-6-yl]-1-methyl-6-trifluoromethyl-2,4(1H,3H)-pyrimidinedione, those compounds I in which $R^1$ signifies methyl, $R^3$, $R^4$, $R^5$ and $R^6$ each signify hydrogen, $R^7$ signifies pentafluoroethyl, n signifies 1, X signifies oxygen and $R^2$ signifies n-propyl, allyl or propargyl, those compounds I in which $R^1$ signifies methyl, $R^3$, $R^4$ and $R^6$ each signify hydrogen, $R^5$ signifies fluorine, $R^7$ signifies pentafluoroethyl, n signifies 1, X signifies oxygen and $R^2$ signifies allyl or propargyl, as well as the corresponding 1,4-benzthiazine derivatives (the above individual compounds of formula I in which the oxygen atom (X) is replaced by a sulphur atom);

those compounds I in which $R^1$ and $R^7$ each signify methyl, $R^5$ signifies fluorine, $R^6$ signifies hydrogen, n signifies zero, X signifies oxygen and $R^2$ signifies ethyl, 2-fluoroethyl, 2-methoxyethyl, cyanomethyl, methoxycarbonylmethyl, 1-methoxycarbonyl-ethyl, 2-methoxycarbony-ethyl, cyclopentyloxycarbonylmethyl, carbamoylmethyl, dimethylcarbamoylmethyl, 3,3-dichloro-2-propenyl, cinnamyl or 3-chloro-2-propynyl, 3-[6-fluoro-2-oxo-3-(2-propynyl)-5-benzoxazolinyl]-1,5,6-trimethyl-2,4(1H,3H)-pyrimidinedione, 1,6-dimethyl-3-[2-oxo-3-(2-propynyl)-5-benzoxazolinyl]-2,4(1H,3H)-pyrimidinedione, 3-[6-chloro-2-oxo-3-(2-propynyl)-5-benzoxazolinyl]-1,6-dimethyl-2,4(1H,3H)-pyrimidinedione, those compounds I in which $R^1$ signifies difluoromethyl, $R^5$ signifies fluorine, $R^6$ signifies hydrogen, $R^7$ signifies methyl, n signifies zero, X signifies oxygen and $R^2$ signifies ethyl, n-propyl, allyl or propargyl, 6-ethyl-1-difluoromethyl-3-[6-fluoro-2-oxo-3-(2-propynyl)-5-benzoxazolinyl]-2,4(1H, 3H)-pyrimidinedione, 1-difluoromethyl-3-[6-fluoro-2-oxo-3-(2-propynyl)-5-benzoxazolinyl]-6-methyl-2,4(1H,3H)-pyrimidinedione, those compounds I in which $R^1$ signifies methyl, $R^5$ signifies fluorine, $R^6$ signifies hydrogen, $R^7$ signifies trifluoromethyl, n signifies zero, X signifies oxygen and $R^2$ signifies ethyl, n-propyl, n-butyl, carbamoylmethyl, allyl or 3-chloro-2-propynyl, those compounds I in which $R^1$ signifies methyl, $R^5$ and $R^6$ each signify hydrogen, $R^7$ signifies trifluoromethyl, n signifies zero, X signifies oxygen and $R^2$ signifies ethyl, n-propyl, 2-fluoroethyl, methoxymethyl, 2-methoxyethyl, cyanomethyl, methoxycarbonylmethyl, 1-methoxycarbonyl-ethyl, 2-methoxycarbonyl-ethyl, cyclopentyloxycarbonylmethyl, carbamoylmethyl, dimethylcarbamoylmethyl, allyl, 3,3-dichloro-2-propenyl, cinnamyl, 1-methyl-2-propynyl or 3-chloro-2-propynyl, 3-[6-chloro-2-oxo-3-(2-propynyl)-5-benzoxazolinyl]-1-methyl-6-trifluoromethyl-2,4(1H,3H)-pyrimidinedione, 1-methyl-3-[2-oxo-3-(2-propynyl)-5-benzoxazolinyl]-6-trifluoromethyl-2,4(1H,3H)-pyrimidinedione, those compounds I in which $R^1$ signifies methyl, $R^5$ and $R^6$ each signify hydrogen, $R^7$ signifies pentafluoroethyl, n signifies zero, X signifies oxygen and $R^2$ signifies n-propyl, allyl or propargyl, those compounds I in which $R^1$ signifies methyl, $R^5$ signifies fluorine, $R^6$ signifies hydrogen, $R^7$ signifies pentafluoroethyl, n signifies zero, X signifies oxygen and $R^2$ signifies allyl or propargyl, as well as the corresponding benzthiazoline derivatives (the above individual benzoxazolines of formula I in which the oxygen atom (X) is replaced by a sulphur atom).

The process in accordance with the invention for the manufacture of the compounds of formula I and their enol ethers as well as salts comprises a) for the manufacture of those compounds of formula I in which $R^1$ signifies hydrogen and $R^6$ signifies hydrogen, fluorine or $C_{1-4}$-alkyl as well as, if desired, of metal salts of these compounds, subjecting a compound of the general formula

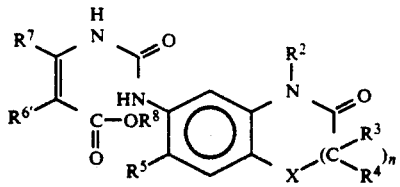

II wherein
$R^2$, $R^3$, $R^4$, $R^5$, $R^7$, n and X have the significances given above,
$R^{6'}$ signifies hydrogen, fluorine or $C_{1-4}$-alkyl and
$R^8$ signifies lower-alkyl, preferably $C_{1-4}$-alkyl, to a cyclization under basic conditions and, if desired, converting a metal salt of the uracil derivative of formula I which may be obtained into the acidic form ($R^1$=hydrogen) by treatment with an acid.

b) for the manufacture of those compounds of formula I in which $R^1$ signifies hydrogen, $R^6$ signifies hydrogen, fluorine or $C_{1-4}$-alkyl and $R^7$ signifies $C_{1-4}$-alkyl as well as of salts of the compounds of formula I, subjecting a compound of the general formula

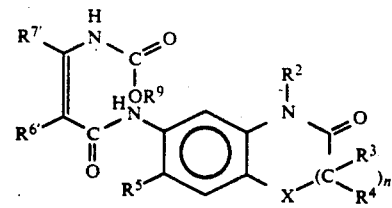

III wherein
$R^2$, $R^3$, $R^4$, $R^5$, $R^{6'}$, n and X have the significances given above,
$R^{7'}$ signifies $C_{1-4}$-alkyl and
$R^9$ signifies lower alkyl, preferably $C_{1-4}$-alkyl, to a cyclization under basic conditions and, if desired, converting a metal salt of the uracil derivative of formula I which may be obtained into the acidic form ($R^1$=hydrogen) by treatment with an acid, c) for the manufacture of those compounds of formula I in which $R^1$ signifies $C_{1-4}$-alkyl, $C_{1-4}$-haloalkyl, $C_{2-5}$-alkenyl or $C_{3-5}$-alkynyl, subjecting a uracil derivative of the general formula

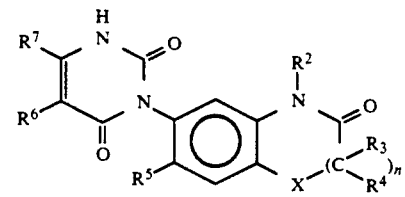

I' wherein $R^2$, $R^3$, $R^4$, $R^5$, $R^6$, $R^7$, n and X have the significances given above,
to an alkylation with an appropriate alkylating agent containing a $C_{1-4}$-alkyl, $C_{2-5}$-alkenyl or $C_{3-5}$-alkynyl group, d) for the manufacture of those compounds of formula I in which $R^2$ signifies hydrogen, cleaving off the protecting group $R^{10}$ in a uracil derivative of the general formula

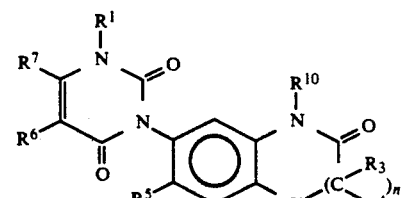

I"

wherein $R^1$, $R^3$, $R^4$, $R^5$, $R^6$, $R^7$, n and X have the significances given above and $R^{10}$ signifies a protecting group, for example isopropyl or tert.butyl, e) for the manufacture of those compounds of formula I in which $R^2$ is different from hydrogen, appropriately alkylating a uracil derivative of the general formula

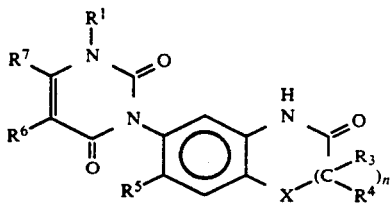

wherein R¹, R³, R⁴, R⁵, R⁶, R⁷, n and X have the significances given above, f) for the manufacture of those compounds of formula I in which R⁶ signifies chlorine, bromine or iodine, chlorinating, brominating or iodinating a uracil derivative of the general formula

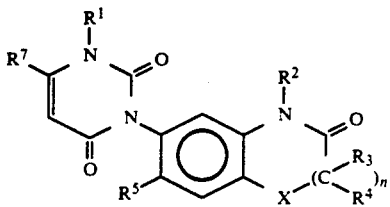

wherein R¹, R², R³, R⁴, R⁵, R⁷, n and X have the significances given above, g) for the manufacture of the enol ethers of formula Ia, treating a pyrimidinone derivative of the general formula

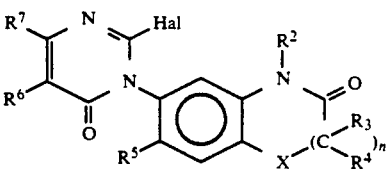

wherein
R², R³, R⁴, R⁵, R⁶, R⁷, n and X have the significances given above
and
Hal signifies chlorine or bromine, with an alkanol, alkenol or alkynol R¹′OH in the presence of an organic base or with the corresponding alcoholate, alkenolate or alkynolate of the general formula

 V wherein R¹′ has the significance given above and M⊕ signifies one equivalent of a metal ion,
and, if desired, converting a thus-obtained compound of formula I in which R¹ signifies hydrogen, R² signifies hydrogen and/or R² signifies $C_{2-5}$-carboxyalkyl into a salt.

The cyclization according to process variant a) can be carried out conveniently by treating the compound of formula II in an inert protic organic solvent such as an alcohol, e.g. methanol, ethanol or isopropanol; an inert aprotic organic solvent such as an aliphatic or cyclic ether, e.g. 1,2-dimethoxyethane, tetrahydrofuran or dioxan, or an aromatic, e.g. benzene or toluene; an inert aprotic, polar organic solvent, e.g. dimethylformamide or dimethyl sulphoxide, whereby such solvents can be used, if desired, in a two-phase mixture with a hydrocarbon, e.g. n-hexane or toluene; or water with a base at temperatures between −78° C. and the reflux temperature of the reaction mixture. As bases there preferably come into consideration sodium alcoholates, alkali metal hydroxides, especially sodium hydroxide and potassium hydroxide, alkali metal carbonates, especially sodium carbonate and potassium carbonate, and sodium hydride. When sodium hydride is used as the base, the solvent is preferably an aliphatic or cyclic ether, dimethylformamide or dimethyl sulphoxide, whereby any of these solvents can be used in admixture with toluene.

After completion of the cyclization the product, when one of the above-mentioned bases is used, is present in the form of the corresponding alkali metal salt. This can be isolated and purified in a manner known per se or the mixture can be acidified in order to isolate the respective compound of formula I itself. A mineral acid such as hydrochloric acid or a strong organic acid such as acetic acid or p-toluenesulphonic acid is preferably used for this purpose.

According to process variant b) the compound of formula III can be cyclized conveniently in an essentially anhydrous inert protic organic solvent such as an alcohol, especially a lower alcohol, e.g. methanol or ethanol, in the presence of a base such as an alkali metal alcoholate, especially the corresponding alcoholate, i.e. methylate or ethylate, of sodium at temperatures between 0° C. and 70° C., preferably in the temperature range of 10° C. to 30° C. Alternatively, for example, the compound III can be cyclized in an essentially anhydrous inert aprotic organic solvent such as e.g. dimethylformamide, N-methylpyrrolidone, tetramethylurea or hexamethylphosphoric acid triamide in the presence of a metal hydride as the base, e.g. sodium hydride or potassium hydride, at temperatures between 0° C. and 70° C., preferably 10° C. to 30° C.

As in the case of process variant a), after completion of the cyclization the product, when one of the above-mentioned bases is used, is present in the form of the corresponding alkali metal salt. This can likewise be isolated and purified in a manner known per se or the mixture can be acidified in order to isolate the respective compound of formula I itself.

In process variant c) the term "alkylation" refers to the substitution of the hydrogen atom of the N¹-atom of the uracil nucleus with a $C_{1-4}$-alkyl, $C_{1-4}$-haloalkyl, $C_{2-5}$-alkenyl or $C_{3-5}$-alkynyl group. As the alkylation agent there is conveniently used a $C_{1-4}$-alkyl, $C_{2-5}$-alkenyl or $C_{3-5}$-alkynyl halide, especially the respective chloride or bromide, or sulphate or a multiply-halogenated $C_{1-4}$-alkane such as, for example, chlorodifluoromethane or a mono- or multiply-halogenated alkene such as, for example, tetrafluoroethene.

The alkylation is conveniently carried out in the presence of an inert, protic organic solvent such as a lower alkanol, e.g. ethanol, optionally in admixture with water; an inert, aprotic organic solvent such as an aliphatic or cyclic ether, e.g. 1,2-dimethoxyethane, tetrahydrofuran or dioxan; a ketone, e.g. acetone or butan-2-one; or an inert, aprotic, polar organic solvent, e.g. dimethylformamide, dimethyl sulphoxide or acetonitrile, as well as in the presence of a base such as sodium hydride, an alkali metal hydroxide, especially sodium or potassium hydroxide, an alkali metal alcoholate, especially sodium alcoholate, or an alkali metal carbonate or bicarbonate, especially sodium carbonate, potassium carbonate, sodium bicarbonate or potassium bicarbonate, at temperatures between 0° C. and the reflux temperature of the reaction mixture, preferably at room temperature, or, in the case of the substitution of the hydrogen atom of the $N^1$-atom with a $C_{1-4}$-haloalkyl group, preferably at temperatures between 50° C. and 100° C. In a preferred embodiment, the uracil derivative of formula I' is treated firstly with the base such as sodium hydride, sodium ethanolate or sodium carbonate in the solvent and, after a short reaction time, treated with the halide in the same solvent. In a further embodiment, the uracil derivative I' is reacted with a dialkyl sulphate in the presence of an alkali metal carbonate, especially sodium carbonate or potassium carbonate, in the solvent, e.g. acetone, at reflux temperature. Depending on the solvent which is used, the reaction has generally finished within a relatively short time or after a few hours. After working-up the reaction mixture the desired end product can be separated from starting materials which may remain and/or byproducts according to methods known per se, e.g. column chromatography and/or fractional crystallization.

The cleavage of the protecting group $R^{10}$ on the nitrogen atom of the oxazolinone, thiazolinone or 3,4-dihydro-3-oxo-2H-1,4-oxa/thiazine ring according to process variant d) is conveniently effected by the action of a strong, essentially anhydrous, inorganic acid such as, for example, sulphuric acid or orthophosphoric acid. Normally, the acid serves not only as the reagent, but also as the solvent, so that no additional solvent is required. The reaction is preferably carried out at temperatures between 80° C. and 160° C., preferably in the temperature range of 120° C. to 150° C.

Process variant e) involves the substitution of the hydrogen atom attached to the heterocyclic nitrogen atom with a $C_{1-4}$-alkyl, $C_{1-4}$-haloalkyl, $C_{1-4}$-alkoxy-$C_{1-4}$-alkyl, $C_{1-4}$-alkoxy-$C_{1-4}$-alkoxy-$C_{1-4}$-alkyl, $C_{2-5}$-cyanoalkyl, $C_{2-5}$-carboxyalkyl, $C_{2-5}$-alkoxycarbonyl-$C_{1-4}$-alkyl, $C_{2-5}$-haloalkoxycarbonyl-$C_{1-4}$-alkyl, $C_{1-4}$-alkoxy-$C_{2-5}$-alkoxycarbonyl-$C_{1-4}$-alkyl, $C_{2-5}$-alkoxycarbonyl-$C_{2-5}$-alkoxycarbonyl-$C_{1-4}$-alkyl, $C_{4-7}$-cycloalkyloxycarbonyl-$C_{1-4}$-alkyl, carbamoyl-$C_{1-4}$-alkyl, mono($C_{1-4}$-alkyl)-carbamoyl-$C_{1-4}$-alkyl, di($C_{1-4}$-alkyl)carbamoyl-$C_{1-4}$-alkyl, $C_{3\,or\,4}$-alkenyl, $C_{3\,or\,4}$-haloalkenyl, cinnamyl, $C_{3\,or\,4}$-alkynyl or $C_{3\,or\,4}$-haloalkynyl group. This "alkylation" can be carried out using a respective halide, especially chloride or bromide, analogously to process variant c). Where a uracil derivative of formula I''' in which $R^1$ signifies hydrogen is used, process variant c) can of course also come into play and respective mixed alkylation products are formed. After working-up the reaction mixture the desired end product can be liberated from any remaining starting materials and from byproducts according to methods known per se, e.g. column chromatography and/or fractional crystallization.

The chlorination or bromination according to process variant f) is conveniently carried out by means of elemental chlorine or sulphuryl chloride or elemental bromine or sulphuryl bromide in the presence of an inert organic solvent such as acetic acid or a chlorinated aliphatic hydrocarbon, e.g. methylene chloride, chloroform or carbon tetrachloride, and in a temperature range of 0° C. to 60° C., preferably at room temperature. Moreover, the reaction can be effected with the aid of an acid-binding agent, for which purpose sodium acetate and tertiary amines such as triethylamine, dimethylaniline and pyridine are especially preferred acid-binding agents.

The iodination according to this process variant is conveniently effected using elemental iodine as the iodinating agent and a low-boiling aliphatic carboxylic acid such as acetic acid as the solvent and at temperatures between about 0° C. and about 110° C., preferably at room temperature. Moreover, it has been found to be convenient to carry out the reaction in the presence of an acid such as fuming nitric acid. In order to eliminate excess iodine, saturated aqueous sodium bisulphite solution can be added after completion of the reaction.

Where in this process variant a uracil derivative of formula I'''' in which $R^1$ and/or $R^2$ signifies an unsaturated aliphatic group such as alkenyl or alkynyl is used, it can happen that not only the unoccupied 5-position of the uracil nucleus is halogenated, but also the mentioned unsaturated aliphatic group is halogenated, e.g. allyl to 2,3-dibromopropyl. Such two different kinds of halogenated products also belong to the scope of the compounds I. After working-up the reaction mixture the desired end product can be liberated from any simultaneously manufactured halogenation products according to methods known per se, e.g. column chromatography and fractional crystallization, or two or more desired halogenation products can be isolated.

In process variant g) the term "metal ion" stands especially for an alkali metal ion, e.g. the sodium or potassium ion, or an alkaline earth metal ion, e.g. the calcium or magnesium ion. The sodium ion is the preferred metal ion. Where the alkanol, alkenol or alkynol $R^{1'}OH$ is used, pyridine is the especially suitable organic base.

The reaction is conveniently effected in an excess of the corresponding hydroxy compound $R^{1'}OH$ as the diluent and at temperatures between 0° C. and 50° C., preferably at room temperature.

Insofar as they are not manufactured directly by the above-described cyclization which is carried out under basic conditions, the desired salts of the compounds of formula I in which $R^1$ signifies hydrogen, $R^2$ signifies hydrogen and/or $R^2$ signifies $C_{2-5}$-carboxyalkyl can also be manufactured from these compounds I in a manner known per se such as, for example, by dissolving the compound of formula I in a solution of a respective inorganic or organic base. The salt formation is generally effected within a short time at room temperature. In one embodiment the sodium salt is manufactured by dissolving the uracil derivative I in aqueous sodium hydroxide solution at room temperature, with equivalent amounts of the uracil derivative and of sodium hydroxide being used. The solid salt can then be isolated by precipitation with a suitable inert solvent or by evaporation of the solvent. A further embodiment comprises introducing an aqueous solution of an alkali metal salt of the uracil derivative I into an aqueous solution of a salt which has a metal ion other than an alkali metal ion, whereby the second metal salt of the uracil derivative is manufactured. This embodiment is generally used for the manufacture of uracil metal salts which are insoluble in water.

The resulting compounds of formula I, enol ethers as well as salts can be isolated and purified according to methods known per se. Further, the sequence in which a possible combination of process variants c)–f) will be conveniently carried out in order to avoid possible undesired concurrent reactions will be familiar to a person skilled in the art.

Insofar as no planned synthesis for the isolation of pure isomers is carried out, the product can result as a mixture of two or more isomers. The isomers can be separated according to methods known per se. If desired, pure optically active isomers can also be manufactured, for example, by synthesis from corresponding optically active starting materials.

The starting materials of formula II are novel and can be produced in a manner known per se, e.g. in accordance with Reaction Scheme 1 hereinafter [methods aa) and bb)] in which $R^2$, $R^3$, $R^4$, $R^5$, $R^{6'}$, $R^7$, $R^{7'}$, $R^8$, n and X have the significances given above:

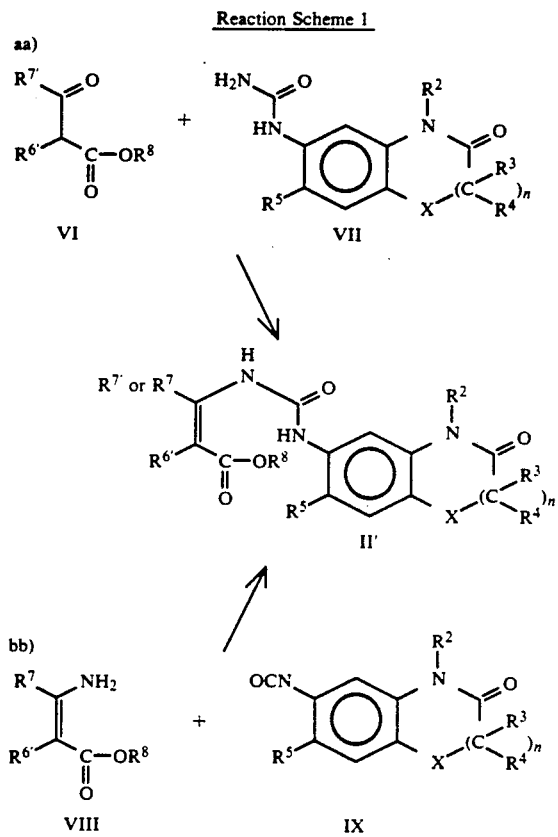

Method aa) is conveniently carried out by reacting the compounds of formulae VI and VII with each other in an essentially anhydrous diluent and in the presence of an acidic catalyst at an elevated temperature. As diluents there especially come into consideration organic solvents which form azeotropes with water, such as aromatics, e.g. benzene, toluene and xylenes; halogenated hydrocarbons such as methylene chloride, chloroform, carbon tetrachloride and chlorobenzene; and aliphatic and cyclic ethers such as 1,2-dimethoxyethane, tetrahydrofuran and dioxan, and as acidic catalysts there especially come into consideration strong mineral acids such as sulphuric acid and hydrochloric acid; organic acids such as p-toluenesulphonic acid; phosphorus-containing acids such as orthophosphoric acid and polyphosphoric acid; and acidic cation exchangers such as "Amberlyst 15" (Fluka). The reaction is generally carried out in a temperature range of about 70° C. to 120° C., preferably at the reflux temperature of the reaction mixture. Under these reaction conditions the desired rapid removal of the water which is formed in the reaction is achieved.

The reaction according to method bb) is conveniently effected in the presence of an essentially anhydrous aprotic organic solvent such as an aliphatic or cyclic ether, e.g. diethyl ether, 1,2-dimethoxyethane, tetrahydrofuran or dioxan, an aliphatic or aromatic hydrocarbon, e.g. n-hexane, benzene, toluene or a xylene; or a halogenated, aliphatic hydrocarbon, e.g. methylene chloride, chloroform, carbon tetrachloride or 1,2-dichloroethane, as well as optionally in the presence of a base, especially an organic tertiary base such as triethylamine or pyridine, whereby the latter can serve not only as the solvent but also as the base, or a metal hydride such as sodium hydride or potassium hydride. The reaction temperatures are preferably in the range of about −80° C. to 50° C., with the reaction being carried out particularly at temperatures between −30° C. and room temperature.

The starting materials of formulae III are also novel. These can be produced by reacting a compound of the general formula

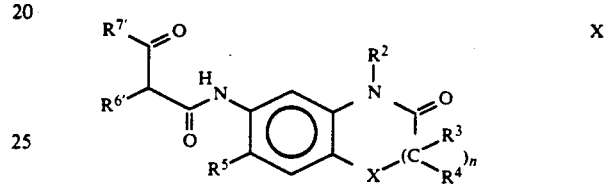

wherein $R^2$, $R^3$, $R^4$, $R^5$, $R^{6'}$, $R^{7'}$, n and X have the significances given above, with a lower alkyl carbamate of the general formula

wherein $R^9$ has the significance given above.

This reaction is conveniently effected in an essentially anhydrous inert aprotic organic solvent in the presence of an acidic catalyst. The reaction mixture is heated at the boiling temperature until water has formed and this is removed continuously from the reaction mixture. As solvents there especially come into consideration organic solvents which form azeotropes with water, such as aromatics, e.g. benzene, toluene and xylenes; and halogenated hydrocarbons, e.g. chloroform, carbon tetrachloride and chlorobenzene, and as acidic catalysts there especially come into consideration organic acids, e.g. toluene-4-sulphonic acid; mineral acids, e.g. sulphuric acid, orthophosphoric acid and polyphosphoric acid; and cation exchangers, e.g. "Amberlyst 15" (Fluka). The heating is generally carried out in a temperature range of about 70° C. to 120° C., preferably at the reflux temperature of the reaction mixture. Under these reaction conditions the desired rapid removal of the water which is formed in the reaction is achieved.

Those uracil derivatives of formulae I', I", I''' and I'''' which are used as starting materials in process variants c) to f) are a sub-group of compounds of formula I which can be produced in accordance with process variant a) or b) and, in the appropriate case, also in accordance with one or more of processes c) to f).

The starting materials of formula IV are novel and can be produced by halogenating the corresponding uracil derivatives of general formula I' given above. In the halogenation there is used as the halogenating agent especially thionyl chloride, phosphorus pentachloride or phosphorus oxychloride or, respectively, phosphorus pentabromide or phosphoryl bromide. If desired, a mixture of phosphorus pentachloride and phosphorus oxychloride or of phosphorus pentabromide and phosphoryl bromide is used, whereby an excess of phosphorus oxychloride or phosphoryl bromide can serve as the diluent. The chlorination or bromination can be carried out in the presence of an inert diluent, especially an aprotic organic solvent such as an aliphatic or aromatic hydrocarbon, e.g. n-hexane, benzene, toluene or a xylene; a halogenated aliphatic hydrocarbon, e.g. methylene chloride, chloroform or 1,2-dichloroethane; a halogenated aromatic hydrocarbon, e.g. chlorobenzene, or a tertiary amine, e.g. N,N-dimethylaniline, but this is not necessary when phosphorus oxychloride or phosphoryl bromide is used as the halogenating agent. When thionyl chloride is used as the halogenating agent, it has been found to be convenient to add a catalytic amount of dimethylformamide. The reaction temperatures generally lie between 0° C. and the reflux temperature of the reaction mixture, preferably between 80° C. and 120° C.

The urea derivatives of formula VII which are used as starting materials in method aa) are novel and can be produced by reacting an amine of the general formula

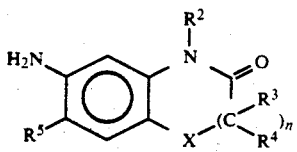

XII wherein $R^2$, $R^3$, $R^4$, $R^5$, n and X have the significances given above,
at room temperature with isocyanic acid in aqueous acetic acid or an aromatic isocyanate of formula IX [see Reaction Scheme 1, method bb)] with ammonia in an inert solvent, e.g. diethyl ether. The production of aromatic ureas is generally known and is described in many literature sources.

The isocyanates of formula IX which are used as starting materials in method bb) and for the production of the urea derivatives VII are also novel and can be produced by treating an amine of formula XII with phosgene. The reaction is conveniently effected in ethyl acetate as the solvent and at temperatures between room temperature and the reflux temperature of the reaction mixture. Also in this case, the production of aromatic isocyanates is generally known and is described in many instances in the literature.

The starting materials of formula X used for the production of the compounds of formula III are also novel. They can be produced, for example, in accordance with Reaction Scheme 2 hereinafter [methods cc), dd) and ee)] in which $R^2$, $R^3$, $R^4$, $R^5$, $R^{6'}$, $R^{7'}$, $R^8$, n and X have the significances given above and $R^{6''}$ signifies hydrogen or $C_{1-4}$-alkyl and $R^{11}$ signifies hydrogen or $C_{1-3}$-alkyl:

Reaction Scheme 2

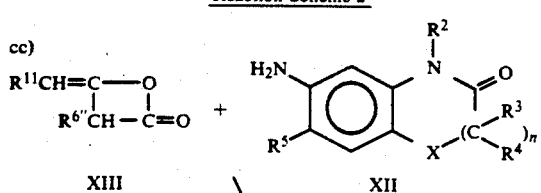

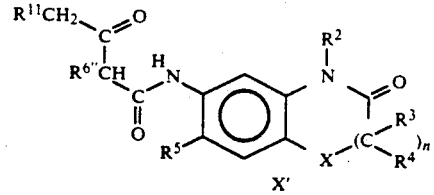

-continued
Reaction Scheme 2

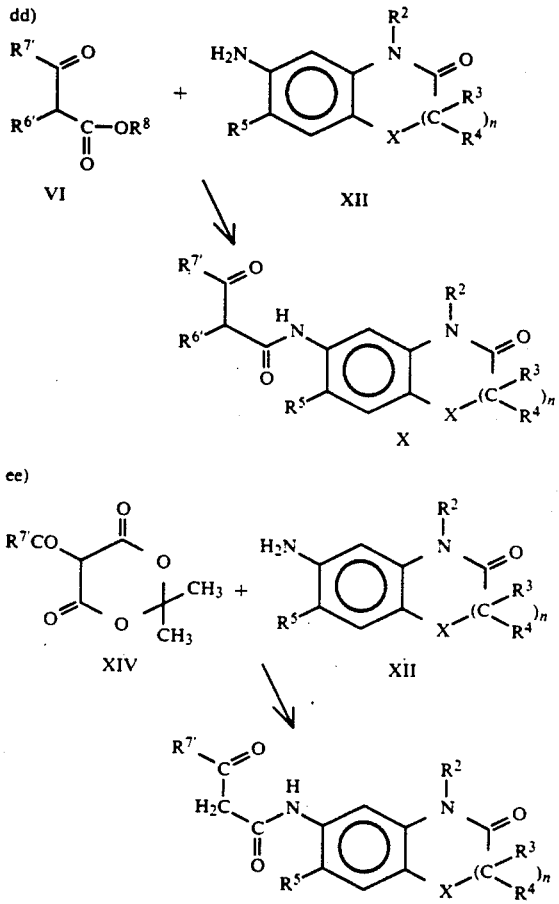

Method cc) is conveniently carried out by reacting the amine of formula XII with the diketene of formula XIII in the presence of an aprotic solvent such as an aromatic hydrocarbon, e.g. benzene or toluene, at temperatures in the range of about 20° to 50° C. Moreover, a basic catalyst, e.g. 4-pyrrolidino-pyridine, is advantageously used.

The reaction according to method dd) is conveniently effected under an excess of the compound of formula VI at temperatures between about 60° C. and the reflux temperature of the reaction mixture. The methyl ester VI ($R^8$ is methyl) is advantageously used.

Method ee) is conveniently effected in an aprotic solvent such as an aromatic hydrocarbon, e.g. toluene or a xylene, at temperatures between 100° C. and 140° C.

The remaining starting materials and, respectively, reagents, namely of formulae V, VI, VIII, XI, XII, XIII and XIV, are either known or can be produced according to methods known per se, see, for example, Houben-Weyl Methoden der organischen Chemie, volume VII/2a, p. 492, and volume VIII, p. 563, J.A.C.S. 69, 1819 (1947), J. Org. Chem. 36, 37 (1971), J.A.C.S. 75, 3152 (1953) and J. Org. Chem. 48, 724 (1983) [compounds VI]; J. Org. Chem. 14, 807 (1949), Helv. Chim. Acta 25, 1311 (1942), J. Org. Chem. 21, 1358 (1956) and J. Org. Chem. 49, 4780 (1984) [compounds VIII]; Japanese Patent Publication No. 221,677 (1987), European Patent Publication No. 170,191 and 218,972 [compounds XII], Houben-Weyl Methoden der organischen Chemie, volume VII/4, pp. 226–263 and J.A.C.S. 69, 2446 (1947) [compounds XIII]; and J. Org. Chem. 43, 2087 (1972) [compounds XIV].

The compounds of formula I as well as their enol ethers and salts (hereinafter collectively referred to as compounds in accordance with the invention or active substances) have herbicidal properties and are suitable for the control of weeds, including weed grasses, inter alia Abutilon theophrasti, Agropyron repens, Alopecurus myosuroides, Amaranthus retroflexus, Avena fatua, Bromus inermis, Cassia obtusifolia, Chenopodium album, Chrysanthemum segetum, Cyperus esculentus, Datura stramonium, Digitaria sanguinalis, Echinochloa crus-galli, Galium aparine, Ipomoea purpurea, Matricaria chamomilla, Poa annua, Setaria faberii, Sinapis arvensis, Sorghum halepense, Stellaria media and Xanthium pennsylvanicum, in diverse crops, for example in cotton, rice, maize, wheat and soya crops. Moreover, the compounds are not only pre-emergence herbicides, but also post-emergence herbicides.

The novel starting materials of formulae II, III, IV, VII, IX and X also have herbicidal properties and can be used for the control of weeds in a similar manner to the compounds I.

In practice, a concentration of 0.01 to 6.0 kg of compound in accordance with the invention/ha, preferably 0.05 to 2.0 kg of compound in accordance with the invention/ha, is sufficient to achieve the desired herbicidal effect.

Furthermore, the compounds can be used for the control of undesired plant growth, e.g. in potatoes, cotton, sunflowers, seed vegetables and aquatic weeds. They can be used, for example, as desiccants to facilitate the harvesting of potatoes and cotton.

The weed control composition in accordance with the invention contains an effective amount of at least one compound of formula I, as defined above, or an enol ether or salt thereof as well as formulation adjuvants. The composition conveniently contains at least one of the following formulation adjuvants: solid carrier substances; solvents or dispersion media; tensides (wetting and emulsifying agents); dispersing agents (without tenside action); and stabilizers. With the use of these and other adjuvants these compounds, namely the herbicidally active substances, can be converted into the usual formulations such as dusts, powders, granulates, solutions, emulsions, suspensions, emulsifiable concentrates, pastes and the like.

The compounds of formula I and their enol ethers are generally insoluble in water, whereas the salts, especially the alkali metal salts and ammonium salts, are generally soluble in water, and can be formulated according to methods which are usual for water-insoluble or water-soluble compounds using the respective formulation adjuvants. The manufacture of the compositions can be carried out in a manner known per se, e.g. by mixing the respective active ingredient with solid carrier substances, by dissolution or suspension in suitable solvents or dispersion media, if necessary using tensides as wetting or emulsifying agents and/or dispersing agents, by diluting pre-prepared emulsifiable concentrates with solvents or dispersion media etc.

As solid carrier substances there essentially come into consideration: natural mineral substances such as chalk, dolomite, limestone, aluminas and silicic acid and salts thereof (for example siliceous earth, kaolin, bentonite, talc, attapulgite and montmorillonite); synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as powders or as granulates.

As solvents or dispersion media there essentially come into consideration: aromatics such as benzene, toluene, xylenes and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol, as well as their ethers and esters; ketones such as acetone, methyl ethyl ketone, methyl isobutyl ketone and cyclohexanone; and strongly polar solvents or dispersion media such as dimethylformamide, N-methylpyrrolidone and dimethyl sulphoxide, such solvents preferably having flash points of at least 30° C. and boiling points of at least 50° C., and water. Among the solvents or dispersion media there also come into consideration so-called liquified gaseous extenders or carrier substances, which are those products which are gaseous at room temperature and under normal pressure. Examples of such products are especially aerosol propellants such as halogenated hydrocarbons, e.g. dichlorodifluoromethane. If the weed control composition in accordance with the invention is present in the form of a pressurized pack, then a solvent is conveniently used in addition to the propellant.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzenesulphonates, e.g. calcium dodecylbenzenesulphonate, and butyl naphthalenesulphonates; and more complex fatty sulphonates, e.g. the amide condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration; lignin, sodium and ammonium salts of lignin sulphonic acids, sodium salts of maleic anhydridge-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides; antioxidants, e.g. gallic acid esters and butylhydroxytoluene; UV-absorbers, e.g. substituted benzophenones, diphenylacrylonitrile acid esters and cinnamic acid esters; and deactivators, e.g. salts of ethylenediaminotetraacetic acid and polyglycols.

The weed control compositions in accordance with the invention can contain, in addition to the active ingredients in accordance with the invention, synergists and other active ingredients, e.g. insecticides, acaricides, fungicides, plant growth regulators and fertilizers. Such combination compositions are suitable for intensifying the activity or for broadening the spectrum of activity.

The weed control compositions in accordance with the invention generally contain between 0.01 and 95 weight percent, preferably between 0.5 and 75 weight percent, of one or more compounds in accordance with the invention as the active ingredient(s). They can be present e.g. in a form which is suitable for storage and transport. In such formulations, e.g. emulsifiable concentrates, the active ingredient concentration is normally in the higher range, preferably between 1 and 50 weight percent, especially between 10 and 20 weight percent. These formulations can then be diluted, e.g. with the same or different inert substances, to give active ingredient concentrations which are suitable for practical use, i.e. preferably about 0.01 to 10 weight percent, especially about 0.5 to 5 weight percent. The active ingredient concentrations can, however, also be smaller or greater.

As mentioned above, the manufacture of the weed control compositions in accordance with the invention can be carried out in a manner known per se.

For the manufacture of pulverous preparations the active ingredient, i.e. at least one compound in accordance with the invention, can be mixed with a solid carrier substance, e.g. by grinding together; or the solid carrier substance can be impregnated with a solution or suspension of the active ingredient and then the solvent or dispersion medium can be removed by evaporation, heating or sucking-off under reduced pressure. By adding tensides or dispersing agents such pulverous preparations can be made readily wettable with water, so that they can be converted into aqueous suspensions which are suitable e.g. as spray compositions.

The active ingredient can also be mixed with a tenside and a solid carrier substance to form a wettable powder which is dispersible in water or it can be mixed with a solid pre-granulated carrier substance to form a product in the form of a granulate.

When desired, the active ingredient can be dissolved in a water-immiscible solvent such as, for example, a high-boiling hydrocarbon, which conveniently contains dissolved emulsifying agent, so that the solution becomes self-emulsifying upon addition to water. Alternatively, the active ingredient can be mixed with an emulsifying agent and the mixture can then be diluted with water to the desired concentration. Moreover, the active ingredient can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the weed control compositions in accordance with the invention, which forms a further object of the present invention, can be carried out according to usual application methods such as sprinkling, spraying, dusting, watering or scattering. The method in accordance with the invention for the control of weeds comprises treating the locus to be protected against weeds and/or the weeds with a compound in accordance with the invention or with a weed control composition in accordance with the invention.

The following Examples serve to illustrate the invention in more detail.

I. MANUFACTURE OF THE COMPOUNDS OF FORMULA I (AND II) AND, RESPECTIVELY, OF THE ENOL ETHERS OF THE COMPOUNDS I

EXAMPLE 1

A solution of 18.51 g of ethyl 3-amino-4,4,4-trifluorocrotonate in 50 ml of dimethylformamide is added dropwise while stirring at 0° C. during 30 minutes to 4.41 g of a 55% sodium hydride dispersion in 100 ml of dimethylformamide and the mixture is stirred at room temperature for 2 hours. The reaction mixture is then cooled to −55° C. and treated during 3 minutes while stirring with a solution of 25.10 g of 6-fluoro-5-isocyanato-3-(2-propynyl)-2-benzothiazolinone in 200 ml of dimethylformamide/toluene (1:1). In so doing, the temperature of the reaction mixture rises to −15° C. and the mixture is subsequently stirred at room temperature for one hour. The thus-formed intermediate 5-{3-[2-(ethoxycarbonyl)-1-trifluoromethyl-vinyl]ureido}-6-fluoro-3-(2-propynyl)-2-benzothiazolinone is not isolated.

The mixture is concentrated to 200 ml at 55° C. under reduced pressure and the residue is poured into a mixture of 700 ml of water and 11 ml of concentrated hydrochloric acid. The aqueous mixture is then extracted with 300 ml of ethyl acetate, the insoluble constituents are filtered off, the organic phase is separated, this phase is washed twice with 400 ml of water each time and dried over anhydrous sodium sulphate. The solution is brought to crystallization by evaporation and the crystals are filtered off under suction and dissolved at 50° C. in 1 l of ethyl acetate. Insoluble constituents are filtered off and the filtrate is evaporated until a viscous oil has formed, the residue is dissolved in 700 ml of diethyl ether and the solution is treated with charcoal and concentrated to 150 ml. The solution is subsequently brought to crystallization with n-hexane while stirring and cooling at 0° C. Finally, the crystals are filtered off under suction, washed with diethyl ether/n-hexane (1:1) and dried.

In this manner there is obtained 3-[6-fluoro-2-oxo-3-(2-propynyl)-5-benzothiazolinyl]-6-trifluoromethyl-2,4(1H,3H)-pyrimidinedione, m.p. 224°–227° C.

EXAMPLE 2

Analogously to the procedure described in Example 1, starting from ethyl 3-amino-4,4,4-trifluorocrotonate and 3,4-dihydro-7-fluoro-6-isocyanato-3-oxo-4-(2-propynyl)-2H-1,4-benzoxazine there is obtained 6-{3-[2-(ethoxycarbonyl)-1-trifluoromethyl-vinyl]ureido}-3,4-dihydro-7-fluoro-3-oxo-4-(2-propynyl)-2H-1,4-benzoxazine (not isolated) and, after cyclization of this benzoxazine, there is obtained 3-[3,4-dihydro-7-fluoro-3-oxo-4-

(2-propynyl)-2H-1,4-benzoxazin-6-yl]-6-trifluoromethyl-2,4(1H,3H)-pyrimidinedione, $^1$H-NMR (CDCl$_3$, 60 MHz): 7.29 ppm (d, 1H), 6.99 ppm (d, 1H), 6.31 ppm (s, 1H), 4.85–4.61 ppm (m, 4H), 2.35 ppm (t, 1H): mass spectrum: m/e 383(20), M+.

EXAMPLE 3

Analogously to the procedure described in Example 1, starting from ethyl 3-amino-4,4,4-trifluorocrotonate and 3,4-dihydro-6-isocyanato-3-oxo-4-(2-propynyl)-2H-1,4-benzoxazine there is obtained 6-{3-[2-(ethoxycarbonyl)-1-trifluoromethyl-vinyl]ureido}-3,4-dihydro-3-oxo-4-(2-propynyl)-2H-1,4-benzoxazine (not isolated) and, after cyclization of this benzoxazine, there is obtained 3-[3,4-dihydro-3-oxo-4-(2-propynyl)-2H-1,4-benzoxazin-6-yl]-6-trifluoromethyl-2,4-(1H,3H)-pyrimidinedione, m.p. >250° C.

EXAMPLE 4

A suspension of 8.2 g of 5-[3-ethoxycarbonylamino)-2-butenoylamino]-6-fluoro-3-(2-propynyl)-2-benzothiazolinone to 100 ml of methanol is treated while stirring at 50° C. with 11.5 ml of a 2N sodium methylate solution and the reaction mixture is stirred for 15 minutes. The solution which thus results is then stirred for 30 minutes, concentrated to 20 ml under reduced pressure and the residue is poured into a solution of 20 ml of 2N hydrochloric acid in 500 ml of water. The resulting precipitate is filtered off under suction, washed with water and dried. In this manner there are obtained 6.1 g of 3-[6-fluoro-2-oxo-3-(2-propynyl)-5-benzothiazolinyl]-6-methyl-2,4(1H,3H)-pyrimidinedione, m.p. >250° C.

EXAMPLES 5-34

The corresponding compound of formula II is in each case cyclized analogously to the procedure described in Example 4 in order to manufacture the compounds of formula I listed in Tables 1a and 1b hereinafter.

TABLE 1a

| Example | R$^2$ | CR$^3$R$^4$ | n | X | Physical data |
|---|---|---|---|---|---|
| 5 | CH$_2$C≡CH | CH$_2$ | 1 | O | $^1$H-NMR (CDCl$_3$, 100 MHz): 7.08 ppm (d, 1H), 6.90 ppm (d, 1H), 5.58 ppm (s, 1H), 4.69–4.64 ppm (m, 4H), 2.33 ppm (t, 1H), 2.18 ppm (s, 3H); m.p. 247–249° C. |
| 6 | CH$_2$CH=CH$_2$ | CH$_2$ | 1 | O | $^1$H-NMR (CDCl$_3$, 400 MHz): 9.89 ppm (s, 1H), 6.98 ppm (d, 1H), 6.82 ppm (d, 1H), 5.83 ppm (m, 1H), 5.66 ppm (s, 1H), 5.22 ppm (m, 2H); 4.69 ppm (s, 2H), 4.52 ppm, (m, 2H), 2.14 ppm (d, 2H), 1.69 ppm (s, 1H); m.p. 141–143° C. |
| 7 | C$_2$H$_5$ | CH(CH$_3$) | 1 | O | M.p. 147–149° C. |
| 8 | CH$_2$C≡CH | CH(CH$_3$) | 1 | O | M.p. 227–230° C. |
| 9 | CH$_3$ | — | Zero | S | M.p. >260° C. |
| 10 | C$_2$H$_5$ | — | Zero | S | M.p. >260° C. |
| 11 | CH$_2$CH=CH$_2$ | — | Zero | S | M.p. >250° C. |
| 12 | CH(CH$_3$)$_2$ | — | Zero | S | M.p. 193–195° C. |
| 13 | nC$_3$H$_7$ | — | Zero | S | M.p. >250° C. |
| 14 | CH(CH$_3$)$_2$ | — | Zero | O | M.p. >250° C. |
| 15 | CH$_3$ | — | Zero | O | M.p. >250° C. |
| 16 | nC$_3$H$_7$ | — | Zero | O | M.p. >250° C. |
| 17 | CH$_2$OCH$_3$ | — | Zero | O | M.p. >250° C. |
| 18 | CH$_2$COOC$_2$H$_5$ | — | Zero | O | M.p. 213–215° C. |
| 19 | CH$_2$CH=CH$_2$ | — | Zero | O | M.p. >250° C. |
| 20 | CH$_2$C≡CH | — | Zero | O | M.p. >250° C. |
| 21 | H | CH$_2$ | 1 | O | M.p. >220° C. |
| 22 | CH$_2$C≡CH | CH$_2$ | 1 | S | M.p. 144–147° C. |

TABLE 1b

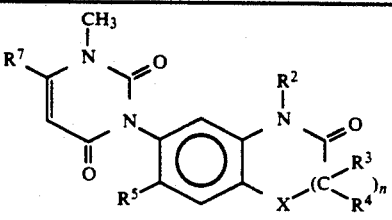

| Example | R² | CR³R⁴ | n | X | R⁷ | Physical data |
|---------|-----|-------|-----|-----|------|---------------|
| 23 | CH(CH₃)₂ | — | Zero | S | C₂H₅ | M.p. 237–238° C. |
| 24 | CH₂CH=CH₂ | CH₂ | 1 | O | C₂H₅ | M.p. 193–200° C. |
| 25 | CH₂CH=CH₂ | CH₂ | 1 | O | nC₃H₇ | M.p. 157–161° C. |
| 26 | CH₂C≡CH | CH₂ | 1 | O | C₂H₅ | M.p. 240° C. (with decomposition) |
| 27 | CH₂C≡CH | CH₂ | 1 | O | nC₃H₇ | M.p. 238–239° C. |
| 28 | CH(CH₃)₂ | CH₂ | 1 | O | C₂H₅ | M.p. 208–210° C. |
| 29 | CH(CH₃)C≡CH | CH₂ | 1 | O | C₂H₅ | Mass spectrum: m/e 357(89) M⁺ |
| 30 | CH(CH₃)C₂H₅ | CH₂ | 1 | O | C₂H₅ | |
| 31 | CH(CH₃)OCH₃ | CH₂ | 1 | O | C₂H₅ | |
| 32 | CH(OCH₃)C₂H₅ | CH₂ | 1 | O | C₂H₅ | |
| 33 | CH(CH₃)CH=CH₂ | CH₂ | 1 | O | C₂H₅ | |
| 34 | CH₂CH=CH₂ | — | Zero | S | C₂H₅ | |

EXAMPLE 35

A suspension of 6.45 g of 6-[3-(ethoxycarbonylamino)-2-pentenoylamino]-3,4-dihydro-7-fluoro-3-oxo-4-(2-propynyl)-2H-1,4-benzoxazine and 3.22 g of sodium methylate in 6.5 ml of methanol is stirred at 62° C. for 4 hours. The solution which thus results is left to stand at room temperature for 64 hours and subsequently poured into a solution of 15 ml of 2N hydrochloric acid in 400 ml of water. The resulting precipitate is filtered off under suction, washed with water and recrystallized from acetone/n-hexane. In this manner there is obtained 6-ethyl-3-[3,4-dihydro-7-fluoro-3-oxo-4-(2-propynyl)-2H-1,4-benzoxazine-6-yl]-2,4(1H,3H)-pyrimidinedione, m.p. 240° C. (with decomposition).

EXAMPLE 36

Analogously to the procedure described in Example 35, by cyclizing 6-[3-(ethoxycarbonylamino)-2-pentenoylamino]-4-allyl-3,4-dihydro-7-fluoro-3-oxo-2H-1,4-benzoxazine there is obtained 6-ethyl-3-(4-allyl-3,4-dihydro-7-fluoro-3-oxo-2H-1,4-benzoxazin-6-yl)-2,4(1H,3H)-pyrimidinedione, m.p. 197°–200° C.

EXAMPLE 37

Analogously to the procedure described in Example 35, by cyclizing 5-[3-(ethoxycarbonylamino)-2-pentenoylamino]-6-fluoro-3-(n-propyl)-2-benzothiazolinone there is obtained 6-ethyl-3-[6-fluoro-2-oxo-3-(n-propyl)-5-benzothiazolinyl]-2,4(1H,3H)-pyrimidinedione, m.p. >250° C.

EXAMPLE 38

A mixture of 27.50 g of 3-[6-fluoro-2-oxo-3-(2-propynyl)-5-benzothiazolinyl]-6-trifluoromethyl-2,4(1H,3H)-pyrimidinedione (see Example 1), 10.80 g of dimethyl sulphate and 9.08 g of sodium carbonate in 250 ml of acetone is heated at the boiling temperature while stirring for 1.5 hours. After cooling the solid constituent is filtered off under suction and washed with acetone. The filtrate is then evaporated to dryness under reduced pressure, the residue is dissolved in 350 ml of ethyl acetate and the solution is washed three times with 300 ml of water each time. Subsequently, the organic phase is dried over anhydrous sodium sulphate and evaporated to dryness under reduced pressure, and the resinous residue is purified by chromatography on 1.5 g of silica gel using ethyl acetate/n-hexane (1:3) as the eluent. The first fraction is recrystallized from ethyl acetate/diethyl ether (1:1), whereby there is obtained 6-fluoro-5-[2-methoxy-6-oxo-4-trifluoromethyl-1(6H)-pyrimidinyl]-3-(2-propynyl)-2-benzothiazolinone, m.p. 191°–192° C. The 2nd fraction is recrystallized from diethyl ether/n-hexane (1:1) and there is thus obtained 3-[6-fluoro-2-oxo-3-(2-propynyl)-5-benzothiazolinyl]-1-methyl-6-trifluoromethyl-2,4(1H,3H)-pyrimidinedione, m.p. 190°–192° C.

EXAMPLES 39–72

The corresponding uracil derivative of formula I' is in each case methylated with dimethyl sulphate analogously to the procedure described in Example 38 in order to manufacture the 1-methyluracils (and in one case also the enol ether) listed in Table 2 hereinafter.

TABLE 2

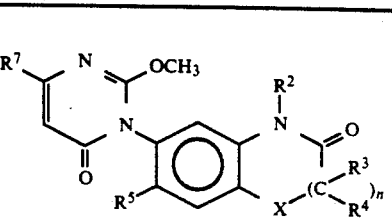

TABLE 2-continued

| Example | Example No. of the starting material I' | Formula: I'''' or Ia' | R² | CR³R⁴ | R⁵ | R⁷ | n | X | Physical data |
|---|---|---|---|---|---|---|---|---|---|
| 39 | 2 | I''''' | CH₂C≡CH | CH₂ | F | CF₃ | 1 | O | ¹H-NMR (CDCl₃, 400 MHz): 7.06 ppm (d, 1H), 6.93 ppm (d, 1H), 6.38 ppm (s, 1H), 4.69 ppm (s, 2H), 4.64 ppm (q, 2H), 3.57 ppm (t, 3H), 2.29 ppm (t, 1H) |
| 40 | 3 | I''''' | CH₂C≡CH | CH₂ | H | CF₃ | 1 | O | M.p. 216–217° C. |
| 41 | 3 | Ia' | CH₂C≡CH | CH₂ | H | CF₃ | 1 | O | M.p. 218–220° C. |
| 42 | 5 | I''''' | CH₂C≡CH | CH₂ | F | CH₃ | 1 | O | ¹H-NMR (CDCl₃, 400 MHz): 7.05 ppm (d, 1H), 6.90 ppm (d, 1H), 5.75 ppm (s, 1H), 4.67 ppm (s, 2H), 4.64 ppm (d, 2H), 3.40 ppm (s, 3H), 2.32 ppm (d, 3H) 2.27 ppm (t, 1H) |
| 43 | 6 | I''''' | CH₂CH=CH₂ | CH₂ | F | CH₃ | 1 | O | ¹H-NMR (CDCl₃, 100 MHz): 6.88 ppm (d, 1H), 6.81 ppm (d, 1H), 5.82 ppm (m, 1H), 5.72 ppm (d, 1H), 5.23 ppm (m, 2H), 4.67 ppm (s, 2H), 4.50 ppm (m, 2H), 3.44 ppm (s, 3H), 2.31 ppm (d, 3H) |
| 44 | 7 | I''''' | C₂H₅ | CH(CH₃) | F | CH₃ | 0 | | M.p. 211–213° C. |

| Example (always formula I''''') | Example No. of the starting material I' | R² | CR³R⁴ | R⁵ | R⁷ | n | X | Physical data |
|---|---|---|---|---|---|---|---|---|
| 45 | 8 | CH₂C≡CH | CH(CH₃) | F | CH₃ | 1 | 1 | M.p. 219–222° C. |
| 46 | 9 | CH₃ | — | F | CH₃ | Zero | S | M.p. 255–257° C. |
| 47 | 10 | C₂H₅ | — | F | CH₃ | Zero | S | M.p. 235–236° C. |
| 48 | 11 | CH₂CH=CH₂ | — | F | CH₃ | Zero | S | M.p. 210–211° C. |
| 49 | 12 | CH(CH₃)₂ | — | F | CH₃ | Zero | S | M.p. 214–216° C. |
| 50 | 13 | nC₃H₇ | — | F | CH₃ | Zero | S | M.p. 222–223° C. |
| 51 | 26/35 | CH₂C≡CH | CH₂ | F | C₂H₅ | 1 | O | M.p. 230° C. (with decomposition) |
| 52 | 24/36 | CH₂CH=CH₂ | CH₂ | F | C₂H₅ | 1 | O | M.p. 172–174° C. |
| 53 | 37 | nC₃H₇ | — | F | C₂H₅ | Zero | S | M.p. 101–102° C. |
| 54 | 14 | CH(CH₃)₂ | — | F | CH₃ | Zero | O | M.p. 143–145° C. |
| 55 | 15 | CH₃ | — | F | CH₃ | Zero | O | M.p. 228–231° C. |
| 56 | 16 | nC₃G₇ | — | F | CH₃ | Zero | O | M.p. 155–157° C. |
| 57 | 17 | CH₂OCH₃ | — | F | CH₃ | Zero | O | M.p. 200–202° C. |
| 58 | 18 | CH₂COOC₂H₅ | — | F | CH₃ | Zero | O | M.p. 167–169° C. |
| 59 | 19 | CH₂CH=CH₂ | — | F | CH₃ | Zero | O | M.p. 164–166° C. |
| 60 | 20 | CH₂≡CH | — | F | CH₃ | Zero | O | M.p. 182–184° C. |
| 61 | 102 | CH₂CN | CH₂ | F | CH₃ | 1 | O | M.p. >230° C. |
| 62 | 22 | CH₂C≡CH | CH₂ | F | CH₃ | 1 | S | M.p. 214–217° C. |
| 63 | 23 | CH(CH₃)₂ | — | F | C₂H₅ | Zero | S | M.p. 176–178° C. |
| 64 | 25 | CH₂CH=CH₂ | CH₂ | F | nC₃H₇ | 1 | O | M.p. 146–147° C. |
| 65 | 27 | CH₂C≡CH | CH₂ | F | nC₃H₇ | 1 | O | M.p. 192–193° C. |
| 66 | 28 | CH(CH₃)₂ | CH₂ | F | C₂H₅ | 1 | O | Mass spectrum: m/e 361(67) M⁺ |
| 67 | 29 | CH(CH₃)C≡CH | CH₂ | F | C₂H₅ | 1 | O | Mass spectrum: m/e 371(98) M⁺ |
| 68 | 30 | CH(CH₃)C₂H₅ | CH₂ | F | C₂H₅ | 1 | O | |
| 69 | 31 | CH(CH₃)OCH₃ | CH₂ | F | C₂H₅ | 1 | O | |
| 70 | 32 | CH(OCH₃)C₂H₅ | CH₂ | F | C₂H₅ | 1 | O | |
| 71 | 33 | CH(CH₃)CH=CH₂ | CH₂ | F | C₂H₅ | 1 | O | |

TABLE 2-continued

| 72 | 34 | CH₂CH=CH₂ | — | F | C₂H₅ | Zero | S |

EXAMPLE 73

A solution of 6.1 g of 3-[6-fluoro-2-oxo-3-(2-propynyl)-5-benzothiazolinyl]-6-methyl-2,4(1H,3H)-pyrimidinedione (see Example 4) in 50 ml of dimethylformamide is added while stirring to a suspension of 0.8 g of a 55% sodium hydride dispersion in 25 ml of dimethylformamide. After the hydrogen evolution has finished the mixture is treated with 2.8 g of dimethyl sulphate and stirred for one hour. Thereafter, the reaction mixture is poured into 500 ml of water, the aqueous mixture is extracted three times with 100 ml of ethyl acetate each time and the organic phase is dried over anhydrous sodium sulphate. The solvent is subsequently distilled off under reduced pressure and the thus-obtained residue (7.2 g) is purified by chromatography on a column of 350 g of aluminium oxide (Brockmann I) using methylene chloride/n-hexane (3:1) as the eluent. The first fraction (1.5 g) is recrystallized from ethyl acetate, whereby there is obtained 1,6-dimethyl-3-[6-fluoro-2-oxo-3-(1,2-propanedienyl)-5-benzothiazolinyl]-2,4(1H,3H)-pyrimidinedione, m.p.>250° C. By further elution of the column with methylene chloride/ethyl acetate (3:1) there is obtained the second fraction (4.7 g) which is recrystallized from ethyl acetate. In this manner there is obtained 1,6-dimethyl-3-[6-fluoro-2-oxo-3-(2-propynyl)-5-benzothiazolinyl]-2,4(1H,3H)-pyrimidinedione, m.p. 180°–181° C.

EXAMPLE 74

A solution of 0.16 ml of bromine in 5 ml of acetic acid is added while stirring at room temperature within 15 minutes to a solution of 1.0 g of 3-[3,4-dihydro-7-fluoro-2-methyl-3-oxo-4-(2-propynyl)-2H-1,4-benzoxazin-6-yl]-1,6-dimethyl-2,4(1H,3H)-pyrimidinedione (see Example 45) in 7 ml of acetic acid and the mixture is stirred at room temperature for 30 minutes. The mixture is then concentrated under reduced pressure, the residue is taken up in ethyl acetate, the solution is washed with dilute, aqueous sodium bicarbonate solution, the organic phase is dried over anhydrous sodium sulphate and concentrated to dryness. In this manner there is obtained 5-bromo-3-[3,4-dihydro-7-fluoro-2-methyl-3-oxo-4-(2-propynyl)-2H-1,4-benoxazin-6-yl]-1,6-dimethyl-2,4(1H,3H)-pyrimidinedione, m.p. 182°–187° C.

EXAMPLES 75–77

The corresponding uracil derivative of formula I'''' is in each case brominated analogously to the procedure described in Example 74 in order to manufacture the 5-bromouracils listed in Table 3 hereinafter.

TABLE 3

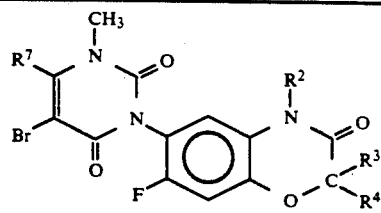

| Example | Example No. of the starting materials I'''' | R² | CR³R⁴ | R⁷ | Physical data |
|---|---|---|---|---|---|
| 75 | 44 | C₂H₅ | CHCH₃ | CH₃ | M.p. 219–220° C. |
| 76 | 52 | CH₂CH=CH₂ | CH₂ | C₂H₅ | M.p. 215–219° C. |
| 77 | 52 | CH₂CHBrCH₂Br | CH₂ | C₂H₅ | M.p. 124–128° C. |

EXAMPLE 78

A solution of 1.08 g of sodium methylate in 10 ml of methanol is added at 20° C. while stirring to a solution of 7.65 g of 6-[2-chloro-6-oxo-4-trifluoromethyl-1(6H)pyrimidinyl]-4-(2-propynyl)-2H-1,4-benzoxazin-3(4H)-one in 300 ml of absolute methanol. A suspension forms during 15 minutes and the temperature rises to 30° C. The reaction mixture is concentrated at 40°–50° C. under reduced pressure and the residue is dissolved in 500 ml of ethyl acetate. The organic phase is washed twice with 200 ml of water each time, dried over anhydrous sodium sulphate and evaporated to dryness under reduced pressure. The crystalline residue is stirred with 20 ml of diethyl ether, cooled to 0° C. and treated with 100 ml of n-hexane. The crystals are filtered off under suction and dried at 50° C. under reduced pressure. In this manner there is obtained 6-[2-methoxy-6-oxo-4-trifluoromethyl-1(6H)-pyrimidinyl]-4-(2-propynyl)-2H-1,4-benzoxazin-3(4H)-one, m.p. 218°–220° C.

EXAMPLE 79

34.94 g of 1,6-dimethyl-3-(6-fluoro-3-isopropyl-2-oxo-5-benzothiazolinyl)-2,4(1H,3H)-pyrimidinedione (see Example 49) are dissolved in 200 ml of concentrated sulphuric acid while stirring and gassing with nitrogen and the solution is heated to 150° C. for 45 minutes. The reaction mixture is cooled to 25° C. and poured on to 1 kg of ice, and the precipitated product is filtered off under suction and washed neutral with water. The filter cake is suspended in 500 ml of ethyl acetate at 60° C., the suspension is concentrated to 250 ml, the product, after cooling, is filtered off under suction, the filtrate is back-washed with ethyl acetate and dried at 50° C. under reduced pressure. In this manner there is obtained 1,6-dimethyl-3-(6-fluoro-2-oxo-5-benzothiazolinyl)-2,4-(1H,3H)-pyrimidinedione, m.p.>250° C.

EXAMPLE 80

Analogously to the procedure described in Example 79, starting from 6-ethyl-3-(6-fluoro-3-isopropyl-2-oxo-5-benzothiazolinyl)-1-methyl-2,4-(1H,3H)-pyrimidinedione (see Example 50) there is obtained 6-ethyl-3-(6-fluoro-2-oxo-5-benzothiazolinyl)-1-methyl-2,4(1H,3H)-pyrimidinedione, m.p. >250° C.

EXAMPLE 81

3.07 g of 1,6-dimethyl-3-(6-fluoro-2-oxo-5-benzothiazolinyl)-2,4(1H,3H)-pyrimidinedione (see Example 79) and 0.48 g of a 55% sodium hydride dispersion are stirred at 25° C. for 1 hour in 50 ml of absolute dimethylformamide. Subsequently, 1.02 g of chloroacetamide are added and the mixture is stirred at 50° C. for 6 hours. The reaction mixture is cooled and treated with 400 ml of water. The precipitated product is filtered off under suction, washed with water and the filter cake is suspended in 200 ml of ethyl acetate at 60° C. The suspension is concentrated to about 50 ml, cooled to 25° C., the solid is filtered off under suction and dried at 50° C. In this manner there is obtained 3-(3-carbamoylmethyl-6-fluoro-2-oxo-5-benzothiazolinyl)-1,6-dimethyl-2,4(1H,3H)-pyrimidinedione, m.p. >260° C.

EXAMPLES 82–101

The corresponding uracil derivative of formula I''' is in each case treated with the corresponding alkylating agent analogously to the procedure described in Example 81 in order to manufacture the compounds of formula I listed in Table 4 hereinafter.

EXAMPLE 102

Analogously to the procedure described in Example 81, by alkylating 3-(3,4-dihydro-7-fluoro-3-oxo-2H-1,4-benzoxazin-6-yl)-6-methyl-2,4(1H,3H)-pyrimidinedione (see Example 21) with chloroacetonitrile there is obtained 3-(2-cyanomethyl-3,4-dihydro-7-fluoro-3-oxo-2H-1,4-benzoxazin-6-yl)-6-methyl-2,4(1H,3H)-pyrimidinedione, m.p. >230° C.

II. PRODUCTION OF THE COMPOUNDS OF FORMULA IX (INTERMEDIATES IN THE MANUFACTURE OF THE COMPOUNDS OF FORMULA I)

EXAMPLE 103

A solution of 22.5 g of 5-amino-6-fluoro-3-(2-propynyl)-2-benzothiazolinone in 350 ml of ethyl acetate is added dropwise at 30° C. during 2 hours while stirring to a solution of 60.0 g of phosgene in 300 ml of ethyl acetate. The resulting suspension is stirred at 50° C. for 2 hours and subsequently heated slowly to the boiling point. The clear solution is then evaporated to dryness and there is thus obtained as the residue 6-fluoro-5-isocyanato-3-(2-propynyl)-2-benzothiazolinone, yellow crystals. This product serves, inter alia, as the starting material in the manufacture of 3-[6-fluoro-2-oxo-3-(2-propynyl)-5-benzothiazolinyl]-6-trifluoromethyl-2,4-(1H,3H)-pyrimidinedione (see Example 1).

EXAMPLE 104

6-Amino-3,4-dihydro-7-fluoro-3-oxo-4-(2-propynyl)-2H-1,4-benzoxazine is treated with phosgene analogously to the procedure described in Example 103 in order to produce the 3,4-dihydro-7-fluoro-6-isocyanato-3-oxo-4-(2-propynyl)-2H-1,4-benzoxazine which is used as the starting material in Example 2. $^1$H-NMR (CDCl$_3$, 60 MHz): 7.02 ppm (d, 1H), 6.88 ppm (d, 1H), 4.88–4.60 ppm (m, 4H), 2.35 ppm (t, 1H).

TABLE 4

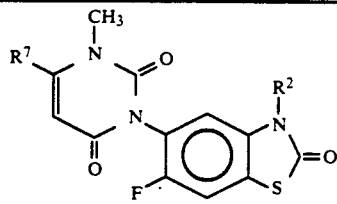

| Example | Example No. of the starting material I''' | R² | R⁷ | Physical data |
|---|---|---|---|---|
| 82 | 79 | isoC₄H₉ | CH₃ | M.p. 168–171° C. |
| 83 | 79 | sec.C₄H₉ | CH₃ | M.p. 135–137° C. |
| 84 | 80 | sec.C₄H₉ | C₂H₅ | M.p. 150–152° C. |
| 85 | 79 | CHF₂ | CH₃ | M.p. 206–208° C. |
| 86 | 79 | CF₂CHF₂ | CH₃ | M.p. 156–158° C. |
| 87 | 79 | CH₂OCH₃ | CH₃ | M.p. 243–245° C. |
| 88 | 80 | CH₂OCH₃ | C₂H₅ | M.p. 198–200° C. |
| 89 | 80 | CH(CH₃)OCH₃ | C₂H₅ | M.p. 221–222° C. |
| 90 | 80 | CH(OCH₃)C₂H₅ | C₂H₅ | M.p. 232–234° C. |
| 91 | 80 | CH(CH₃)OC₂H₅ | C₂H₅ | M.p. 216–218° C. |
| 92 | 79 | CH₂CN | CH₃ | M.p. 247–250° C. |
| 93 | 79 | CH₂COOC₂H₅ | CH₃ | M.p. 193–195° C. |
| 94 | 79 | CH₂CON(CH₃)₂ | CH₃ | M.p. 257–258° C. |
| 95 | 79 | CH₂C(CH₃)=CH₂ | CH₃ | M.p. 203–205° C. |
| 96 | 79 | CH(CH₃)CH=CH₂ | CH₃ | M.p. 148–178° C. |
| 97 | 80 | CH(CH₃)CH=CH₂ | C₂H₅ | M.p. 124–134° C. |
| 98 | 79 | Cinnamyl | CH₃ | M.p. 125–160° C. |
| 99 | 80 | CH₂C≡CH | C₂H₅ | M.p. >250° C. |
| 100 | 79 | CH(CH₃)C≡CH | CH₃ | M.p. 184–186° C. |
| 101 | 80 | CH(CH₃)C≡CH | C₂H₅ | M.p. 177–179° C. |

EXAMPLE 105

6-Amino-3,4-dihydro-3-oxo-4-(2-propynyl)-2H-1,4-benzoxazine is treated with phosgene analogously to the procedure described in Example 103 in order to produce the 3,4-dihydro-6-isocyanato-3-oxo-4-(2-propynyl)-2H-1,4-benzoxazine which is used as the starting material in Example 3. $^1$H-NMR (CDCl$_3$, 400 MHz): 6.98-6.92 ppm (m, 2H), 6.79 ppm (q, 1H), 4.66 ppm (d, 2H), 4.63 ppm (s, 2H), 2.31 ppm (t, 1H).

III. PRODUCTION OF THE COMPOUNDS OF FORMULAE X AND III (INTERMEDIATES IN THE MANUFACTURE OF THE COMPOUNDS OF FORMULA I)

EXAMPLE 106

A suspension of 4.7 g of 5-amino-6-fluoro-3-(2-propynyl)-2-benzothiazolinone, 1.93 g of diketene and 0.05 g of 4-pyrrolidinopyridine in 250 ml of benzene is stirred at room temperature for 30 minutes and subsequently held at 50° C. for 30 minutes. In this manner there is obtained a solution of 5-acetoacetylamino-6-fluoro-3-(2-propynyl)-2-benzothiazolinone which is used as such in the next reaction step without isolation of the product.

The above clear solution is heated to the boiling point under a water separator for 2.5 hours with 2.85 g of ethyl carbamate and 0.2 g of p-toluenesulphonic acid monohydrate. Subsequently, the mixture is again treated with 0.2 g of p-toluenesulphonic acid monohydrate and heated for a further 2.5 hours. The reaction mixture is evaporated to dryness under reduced pressure. The thus-obtained crude product (11.7 g) is suspended with 50 ml of diethyl ether, the insoluble portion is filtered off under suction and dried. In this manner there are obtained 8.2 g of 5-[3-ethoxycarbonylamino)-2-butenoylamino]-6-fluoro-3-(2-propynyl)-2-benzothiazolinone, m.p. about 167°-169° C. This product serves, inter alia, as the starting material in the manufacture of 3-[6-fluoro-2-oxo-3-(2-propynyl)-5-benzothiazolinyl]-6-methyl-2,4(1H,3H)-pyrimidinedione (see Example 4).

EXAMPLE 107-134

Analogously to the procedure described in Example 106, the corresponding amine of formula XII is reacted with the corresponding diketene in order to produce the corresponding compound of formula X' which, in turn, is reacted with ethyl carbamate in order to produce the compounds of formula III listed in Tables 5a and 5b hereinafter. In these Tables there are given in each case both intermediates (formula X''' or X'''' and, respectively, III' or III'') as well as the respective end product I to which the corresponding intermediate of formula III' or III'' leads by ring closure.

TABLE 5a

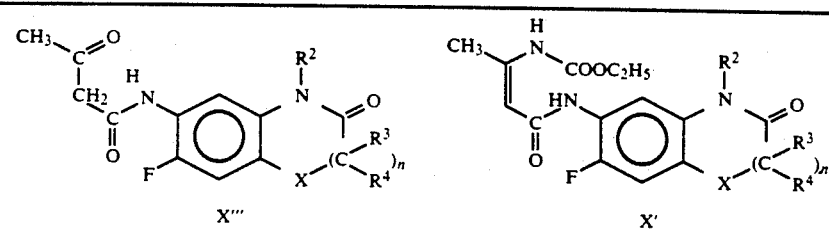

| Example | Example No. of the end product I | R$^2$ | (CR$^3$R$^4$) | n | X | Physical data Compound X''' | Compound III' |
|---|---|---|---|---|---|---|---|
| 107 | 5 | CH$_2$C≡CH | CH$_2$ | 1 | O | —(not isolated) | (—not isolated) |
| 108 | 6 | CH$_2$CH=CH$_2$ | CH$_2$ | 1 | O | " | M.p. 175-177° C. |
| 109 | 7 | C$_2$H$_5$ | CH(CH$_3$) | 1 | O | " | M.p. 192-194° C. |
| 110 | 8 | CH$_2$C≡CH | CH(CH$_3$) | 1 | O | " | M.p. 171-173° C. |
| 111 | 9 | CH$_3$ | — | Zero | S | M.p. 150-151° C. | M.p. 250-251° C. |
| 112 | 10 | C$_2$H$_5$ | — | Zero | S | M.p. 118-120° C. | M.p. 195-197° C. |
| 113 | 11 | CH$_2$CH=CH$_2$ | — | Zero | S | M.p. 113-115° C. | M.p. 194-196° C. |
| 114 | 12 | CH(CH$_3$) | — | Zero | S | M.p. 166-167° C. | M.p. 186-187° C. |
| 115 | 13 | nC$_3$H$_7$ | — | Zero | S | M.p. 116-117° C. | M.p. 203-205° C. |
| 116 | 14 | CH(CH$_3$)$_2$ | — | Zero | O | M.p. 167-169° C. | M.p. 186-188° C. |
| 117 | 15 | CH$_3$ | — | Zero | O | M.p. 137-139° C. | M.p. 200-202° C. |
| 118 | 16 | nC$_3$H$_7$ | — | Zero | O | M.p. 105-107° C. | M.p. 159-160° C. |
| 119 | 17 | CH$_2$OCH$_3$ | — | Zero | O | M.p. 126-128° C. | M.p. 181-183° C. |
| 120 | 18 | CH$_2$COOC$_2$H$_5$ | — | Zero | O | M.p. 143-145° C. | M.p. 184-185° C. |
| 121 | 19 | CH$_2$CH=CH$_2$ | — | Zero | O | M.p. 106-107° C. | M.p. 149-151° C. |
| 122 | 20 | CH$_2$C≡CH | — | Zero | O | M.p. 114-116° C. | M.p. 199-200° C. |
| 123 | 21 | H | CH$_2$ | 1 | O | M.p. >230° C. | $^1$H-NMR (CDCl$_3$, 200 MHz): 11.50 ppm (s, 1H), 10.66 ppm (s, 1H), 9.62 ppm (s, 1H), 7.56 ppm (d, 1H), 6.96 ppm (d, 1H), 5.30 ppm (s, 1H), 4.57 ppm (s, 2H), 4.30 ppm (q, 2H), 2.26 ppm (s, 3H), 1.22 ppm (t, 3H) |
| 124 | 22 | CH$_2$C≡CH | CH$_2$ | 1 | S | —(not isolated) | M.p. 185-188° C. |

TABLE 5b

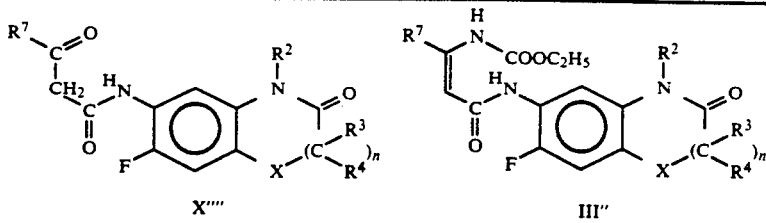

| Example | Example No. of the end product I | R² | (CR³R⁴) | n | X | R⁷ | Physical data Compound X'''' | Compound III'' |
|---|---|---|---|---|---|---|---|---|
| 123 | 23 | CH(CH₃)₂ | — | Zero | S | C₂H₅ | M.p. 167–168° C. | M.p. 150–152° C. |
| 124 | 24 | CH₂CH=CH₂ | CH₂ | 1 | O | C₂H₅ | —(not isolated) | M.p. 109–115° C. |
| 125 | 25 | CH₂CH=CH₂ | CH₂ | 1 | O | nC₃H₇ | —(not isolated) | M.p. 86–88° C. |
| 126 | 26 | CH₂C≡CH | CH₂ | 1 | O | C₂H₅ | M.p. 113–115° C. | M.p. 132–133° C. |
| 127 | 27 | CH₂C≡CH | CH₂ | 1 | O | nC₃H₇ | M.p. 88–93° C. | M.p. 143–147° C. |
| 128 | 28 | CH(CH₂)₂ | CH₂ | 1 | O | C₂H₅ | —(not isolated) | —(not isolated) |
| 129 | 29 | CH(CH₃)C≡CH | CH₂ | 1 | O | C₂H₅ | M.p. 110–114° C. | —(not isolated) |
| 130 | 30 | CH(CH₃)C₂H₅ | CH₂ | 1 | O | C₂H₅ | | |
| 131 | 31 | CH(CH₃)OCH₃ | CH₂ | 1 | O | C₂H₅ | | |
| 132 | 32 | CH(OCH₃)C₂H₅ | CH₂ | 1 | O | C₂H₅ | | |
| 133 | 33 | CH(CH₃)CH=CH₂ | CH₂ | 1 | O | C₂H₅ | | |
| 134 | 34 | CH₂CH=CH₂ | — | Zero | S | C₂H₅ | | |

EXAMPLE 135

A solution of 11.0 g of 2,2-dimethyl-5-propionyl-1,3-dioxane-4,6-dione in 50 ml of toluene is added dropwise at 30° C. during 15 minutes while stirring to a solution of 12.2 g of 6-amine-3,4-dihydro-7-fluoro-3-oxo-4-(2-propynyl)-2H-1,4-benzoxazine in 100 ml of toluene. The reaction mixture (still a solution) is stirred at 124° C. for 4 hours and thereafter left to stand at room temperature for about 16 hours. Then, the precipitated crystals are separated and dried.

In this manner there is obtained 3,4-dihydro-7-fluoro-3-oxo-4-(2-propynyl)-6-propioacetylamino-2H-1,4-benzoxazine, m.p. 113°–115° C.

A suspension of the above intermediate, 6.14 g of ethyl carbamate and 0.2 g of p-toluenesulphonic acid monohydrate in 260 ml of benzene is heated at the boiling temperature under a water separator for 2.5 hours. Subsequently, the mixture is again treated with 0.2 g of p-toluenesulphonic acid monohydrate and heated for a further 2.5 hours. The reaction mixture is evaporated to dryness under reduced pressure, whereby 25.5 g of crude product are obtained. This is suspended with 200 ml of ethyl acetate, washed with 300 ml of water and crystallized from ethyl acetate. In this manner there are obtained 7.2 g of 6-[3-(ethoxycarbonylamino)-2-pentenoylamino]-3,4-dihydro-7-fluoro-3-oxo-4-(2-propynyl)-2H-1,4-benzoxazine, m.p. 133° C. (with decomposition). This product serves as the starting material in the manufacture of 6-ethyl-3-[3,4-dihydro-7-fluoro-3-oxo-4-(2-propynyl)-2H-1,4-benzoxazin-6-yl]-2,4(1H,3H)-pyrimidinedione (see Example 35).

EXAMPLE 136

Analogously to the procedure described in Example 47, 4-allyl-6-amino-3,4-dihydro-7-fluoro-3-oxo-2H-1,4-benzoxazine is reacted with 2,2-dimethyl-5-propionyl-1,3-dioxane-4,6-dione in order to produce 4-allyl-3,4-dihydro-7-fluoro-3-oxo-6-propioacetylamino-2H-1,4-benzoxazine, mass spectrum (m/e): 320(95), M⁺, and this can be reacted with ethyl carbamate in order to produce the 6-[3-(ethoxycarbonylamino)-2-pentenoylamino]-4-allyl-3,4-dihydro-7-fluoro-3-oxo-2H-1,4-benzoxazine, m.p. 115° C. (with decomposition), which is used as the starting material in Example 36.

EXAMPLE 137

Analogously to the procedure described in Example 135, 5-amino-6-fluoro-3-(n-propyl)-2-benzothiazolinone is reacted with 2,2-dimethyl-5-propionyl-1,3-dioxane-4,6-dione in order to produce 6-fluoro-5-propioacetylamino-3-(n-propyl)-2-benzothiazolinone, m.p. 87°–88° C., and this can then be reacted with ethyl carbamate in order to produce the 5-[3-(ethoxycarbonylamino)-2-pentenoylamino]-6-fluoro-3-(n-propyl)-2-benzothiazolinone, m.p. 174°–175° C., which is used as the starting material in Example 37.

IV. PRODUCTION OF THE COMPOUNDS OF FORMULA IV

EXAMPLE 138

16.61 g of pyridine are added at 25° C. while stirring to a suspension of 25.55 g of 3-[3,4-dihydro-3-oxo-4-(2-propynyl)-2H-1,4-benzoxazin-6-yl]-6-trifluoromethyl-2,4(1H,3H)-pyrimidinedione (see Example 3) and 32.13 g of phosphorus oxychloride in 250 ml of toluene. The reaction mixture is heated to 100° C. for 6 hours, cooled to 25° C. and poured on to 500 g of ice. Subsequently, the aqueous mixture is extracted three times with 150 ml of ethyl acetate each time and the organic phase is washed neutral with water, dried over anhydrous sodium sulphate and evaporated to dryness under reduced pressure. The resinous product is purified by chromatography on a silica gel column with ethyl acetate/n-hexane (1:3) as the eluent. Finally, the product is recrystallized from diethyl ether/n-hexane. In this manner there is obtained 6-[2-chloro-6-oxo-4-trifluoromethyl-1(6H)-pyrimidinyl]-4-(2-propynyl)-2H-1,4-benzoxazin-3(4H)-one, m.p. 143°–145° C. (see Example 78).

EXAMPLE 139

Preparation of compounds of the formula I, in which $R^6$ is $C_{1-4}$-alkyl

Compounds of the formula I, in which $R^6$ is $C_{1-4}$-alkyl can also be prepared according to the following reaction scheme ($R^6$ is methyl):

Preparation of 3-[6-fluoro-2-oxo-3-(2-butinyl)-5-benzothiazolinyl]-2,5-dimethyl-6-triflurormethyl-2,4(1H,3H)-pyrimidindione a) Preparation of ethyl-3-amino-2-methyl-4,4,4-trifluor-acetoacetate Anhydrous gaseous ammonia is introduced continuously into 59,4 g ethyl-2-methyl-4,4,4-trifluor-acetoacetate in 100 ml toluene which is heated under reflux until the reaction is complete. The solvent is subsequently distilled off and the thus-obtained residue is distilled at 290 mBar pressure and at a temperature of 132° C. In

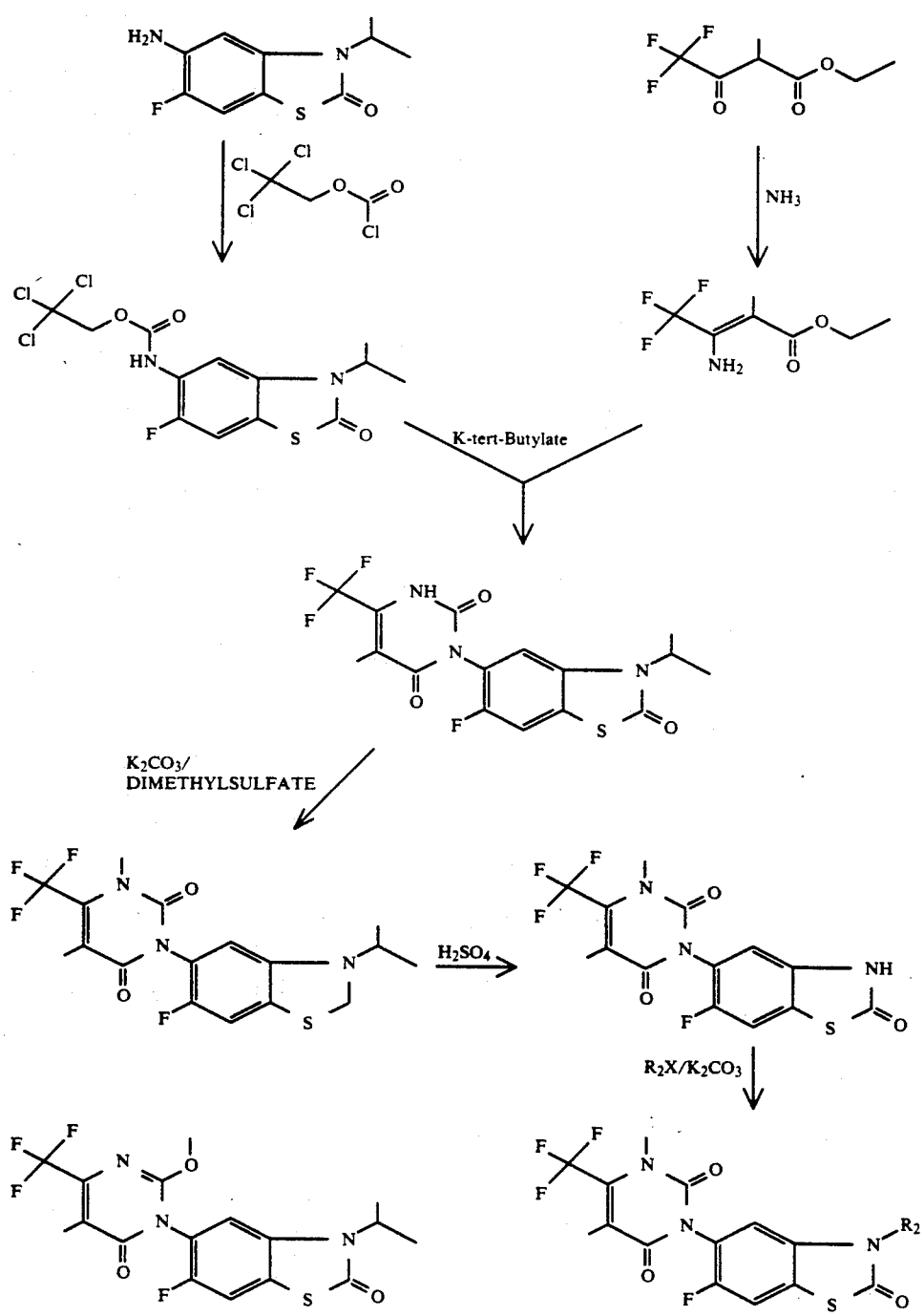

this manner there is obtained ethyl-3-amino-2-methyl-4,4,4-trifluor-acetoacetate: $n_D^{21}$: 1,4326.

b) Preparation of 5-[(2,2,2-trichoroethoxy)carbamino]-6-fluor-3-(2-propinyl)-2-benzthiazolinone 30 g 6-Fluor-5-amino-3-(2-propinyl)-2-benzthiazolinone is solved in 200 ml methylenchloride. treated with 10,5 g pyridine and cooled to −5° C. Subsequently, 28,09 g 2,2,2-trichloroethyl chloroformiate solved in 50 ml methylene chloride is added dropwise. The reaction mixture is stirred for 15 minutes and then poured into 200 ml of water. The organic phase is separated and treated with 50 g silica gel. The silicagel is then filtered and washed with 50 ml methylene chloride. Subsequently, the filtrate is concentrated and the crystallized product is dried under reduced pressure.

Mass spectra data: m/e 402, 400, 360, 358, 252, 210, 183.

c) Preparation of 3-[6-fluoro-2-oxo-3-(2-propinyl)-5-benzothiazolinyl]-5-methyl-6-trifluoromethyl-2,4(1H,3H)-pyrimidindion 34,2 g ethyl-3-amino-4,4,4-trifluoro-2-methylcrotonate is solved in 150 ml dimethylformamide and treated under cooling within 10 minutes with 20 g potassium-tert-butylate. 68,3 g 5-[(2,2,2-trichoroethoxy)carbamino]-6-fluor-3-(2-propinyl)-2-benzthiazolinone solved in 150 ml dimethyl formamide is added after 60 minutes of stirring. The reaction mixture is then heated to 60° C. erhitzt and stirred for 2½ hours at this temperature. Thereafter, the reaction mixture is poured into 600 ml water, acidified, and then extracted two times with 200 ml of ethyl acetate each time. The organic phase is washed with 5% by weight of NaCl-solution to neutrality and concentrated. The thus-obtained residue is purified by chromatography with 100 g silica gel using hexane:ethyl acetate (7:3), m.p. 201°–206° C.

d) Preparation of 3-[6-fluoro-2-oxo-3-(2-propinyl)-5-benzothiazolinyl]-1,5-dimethyl-6-trifluoromethyl-2,4(1H,3H)-pyrimidindion 29,6 g of 3-[6-fluoro-2-oxo-3-(2-propinyl)-5-benzothiazolinyl]-5-methyl-6-trifluoromethyl-2,4(1H,3H)-pyrimidindion in 200 ml acetonitrile is stirred with 9,25 g dimethylsulfate and 10,14 g potassium carbonate at 40° C. for 90 minutes. Thereafter, the reaction mixture is poured into 200 ml of water and extracted two times with 200 ml ethyl acetate each time. The organic phase is subsequently concentrated. The thus-obtained residue is purified by chromatography with 400 g silica gel using hexane:ethyl acetate (7:3).

Two products are isolated:

1. 6-fluoro-5-[2-methoxy-5-methyl-6-oxo-4-trifluormethyl-1(6H)-pyrimidinyl]-3-(2-propinyl)-2-benzothiazolinone as colourless oil.

Mass spectra data: m/e 417, 375, 356, 207.

$H^1$-NMR (200 MHz, $CDCl_3$): 7,34 (d, 1p); 4,5 (m, 1p); 3,97 (s, 3p); 2,22 (m, 3p); 1,57 (d, 6p).

2. 3-[6-fluoro-2-oxo-3-(2-propinyl)-5-benzothiazolidinyl]-1,5-dimethyl-6-trifluormethyl-2,4(1H,3H)-pyrimidindione, F: 171°–173° C., from n-hexane-ethyl acetate.

Mass spectra data: m/e 417, 375, 210, 43.

$H^1$-NMR (200 MHz, $CDCl_3$): ppm 7,34 (d, 1p); 7,24 (d, 1p); 4,7 (m, 1p); 3,58 (m, 3p); 2,26 (q, 3p); 1,57 (d, 6p).

Preparation of 3-[6-fluoro-2-oxo-5-benzothiazolinyl]-2,5-dimethyl-6-triflurormethyl-2,4(1H,3H)-pyrimidindione 5,63 g of 3-[6-fluoro-2-oxo-3-(2-propinyl)-5-benzothiazolidinyl]-1,5-dimethyl-6-trifluormethyl-2,4(1H,3H)-pyrimidindione is stirred for 3 hours at a temperature of 130° C. in concentrated sulfuric acid. The reaction mixture is poured into 200 ml of ice water and the precipitated product is filtered off under suction and washed to neutrality.

Mass spectra data: m/e 375, 210, 166, 96

$^1$H-NMR (200 MHz, $CDCl_3$): ppm 9,28 (s, with $D_2O$ interchangeable, 1p); 7,29 (d, 1p); 6,80 (d, 1p); 3,59 (m, 3p); 2,27 (m, 3p).

e) Preparation of 3-[6-fluoro-2-oxo-3-(2-butyl)-5-benzothiazolinyl]-2,5-dimethyl-6-triflurormethyl-2,4(1H,3H)-pyrimidindione 2,5 g of 3-[6-fluoro-2-oxo-5-benzothiazolinyl]-2,5-dimethyl-6-triflurormethyl-2,4(1H,3H)-pyrimidindione, 1,42 g of 3-chloro-1-butine, 0.93 g potassiumcarbonate and a catalytic amount of potassium jodide are stirred for 8 hours under reflux in 10 ml acetonitrile. Thereafter, the reaction mixture is poured into 50 ml of water and extracted two times with 25 ml ethyl acetate each time. The organic phase is washed to neutrality and subsequently concentrated. The thus-obtained residue is purified by chromatography with 30 g silica gel using hexane: ethyl acetate (8:2) and the product is recrystallized from hexane/ethyl acetate. m.p. 188°–190° C.

Mass spectra data: m/e 427, 399, 375, 210

$H^1$-NMR (200 MHz, $CDCl_3$): ppm 7,50 (d, 1p); 7,36 (d, 1p); 5,72 (m, 1p); 3,59 (m, 3p); 2,49 (d, 1p); 2,26 (m, 3p); 1,66 (d, 3p).

Analogously to the procedure described in Example 139 a)-e) the following compounds of the formula I are prepared:

TABLE A

Compounds of the formula:

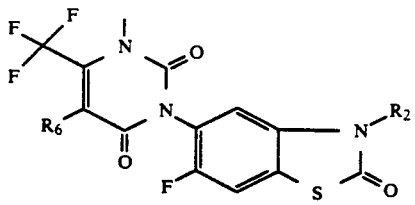

| $R_2$ | $R_6$ | Phys. data |
|---|---|---|
| $CH(CH_3)CH=CH_2$ | $CH_3$ | m.p. 180–182° C. |
| $CH(CH_3)CH_2CH_3$ | $CH_3$ | m.p. 173–175° C. |
| $CH(CH_3)OCH_3$ | $CH_3$ | m.p. >200° C. (decomp.) |
| $CH(CH_3)C\equiv CH$ | $C_2H_5$ | |
| $CH(CH_3)CH=CH_2$ | $C_2H_5$ | |
| $CH(CH_3)CH_2CH_3$ | $C_2H_5$ | |
| $CH(CH_3)OCH_3$ | $C_2H_5$ | |
| $CH_2C\equiv CH$ | $C_2H_5$ | |
| $CH(CH_3)C\equiv CH$ | n-Propyl | |
| $CH(CH_3)CH_2CH_3$ | n-Propy | |
| $CH(CH_3)C\equiv CH$ | i-Propyl | |
| $CH(CH_3)CH_2CH_3$ | i-Propyl | |
| $CH(CH_3)C\equiv CH$ | n-Butyl | |
| $CH(CH_3)CH_2CH_3$ | n-Butyl | |
| $CH(CH_3)C\equiv CH$ | sec-Butyl | |

TABLE B

Compounds of the formula:

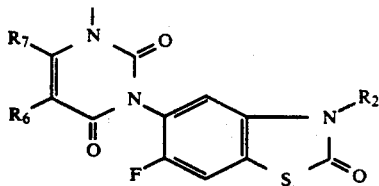

| R₂ | R₆ | R₇ | Phys. data |
|---|---|---|---|
| CH(CH₃)CH≡CH | CH₃ | CH₃ | |
| CH(CH₃)CH₂CH₃ | CH₃ | CH₃ | |
| CH(CH₃)OCH₃ | CH₃ | CH₃ | |
| CH(CH₃)C≡CH | C₂H₅ | CH₃ | |
| CH(CH₃)CH=CH₂ | C₂H₅ | CH₃ | |
| CH(CH₃)CH₂CH₃ | C₂H₅ | CH₃ | |
| CH(CH₃)OCH₃ | C₂H₅ | CH₃ | |
| CH₂C≡CH | C₂H₅ | CH₃ | |
| CH(CH₃)C≡CH | n-Propyl | CH₃ | |
| CH(CH₃)CH₂CH₃ | n-Propyl | C₂H₅ | |
| CH(CH₃)C≡CH | i-Propyl | CH₃ | |
| CH(CH₃)CH₂CH₃ | i-Propyl | C₂H₅ | |
| CH(CH₃)C≡CH | n-Butyl | CH₃ | |
| CH(CH₃)CH₂CH₃ | n-Butyl | C₂H₅ | |
| CH₂C≡CH | C₂H₅ | C₂H₅ | |

TABLE C

Compounds of the formula:

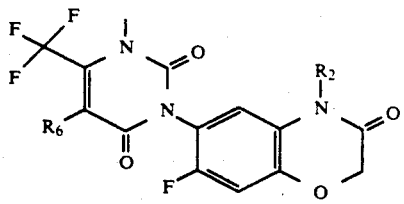

| R₂ | R₆ | Phys. data |
|---|---|---|
| CH(CH₃)CH≡CH | CH₃ | m.p. >200° C. (decomp.) |
| CH(CH₃)CH₂CH₃ | CH₃ | |
| CH(CH₃)OCH₃ | CH₃ | |
| CH(CH₃)C≡CH | C₂H₅ | |
| CH(CH₃)CH=CH₂ | C₂H₅ | |
| CH(CH₃)CH₂CH₃ | C₂H₅ | |
| CH(CH₃)OCH₃ | C₂H₅ | |
| CH(CH₃)C≡CH | n-Propyl | |
| CH(CH₃)CH₂CH₃ | n-Propy | |
| CH(CH₃)C≡CH | i-Propyl | |
| CH(CH₃)CH₂CH₃ | i-Propyl | |
| CH(CH₃)C≡CH | n-Butyl | |
| CH(CH₃)CH₂CH₃ | n-Butyl | |
| CH(CH₃)C≡CH | sec-Butyl | |

TABLE D

Compounds of the formula:

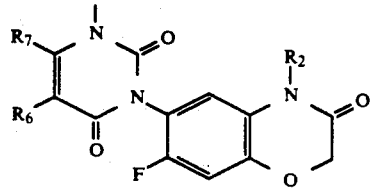

| R₂ | R₆ | R₇ | Phys. data |
|---|---|---|---|
| CH(CH₃)CH≡CH | CH₃ | CH₃ | |

TABLE D-continued

Compounds of the formula:

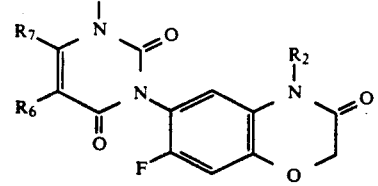

| R₂ | R₆ | R₇ | Phys. data |
|---|---|---|---|
| CH(CH₃)CH₂CH₃ | CH₃ | CH₃ | |
| CH(CH₃)OCH₃ | CH₃ | CH₃ | |
| CH(CH₃)C≡CH | C₂H₅ | CH₃ | |
| CH(CH₃)CH=CH₂ | C₂H₅ | CH₃ | |
| CH(CH₃)CH₂CH₃ | C₂H₅ | CH₃ | |
| CH(CH₃)OCH₃ | C₂H₅ | CH₃ | |
| CH₂C≡CH | C₂H₅ | CH₃ | |
| CH(CH₃)C≡CH | n-Propyl | CH₃ | |
| CH(CH₃)CH₂CH₃ | n-Propyl | C₂H₅ | |
| CH(CH₃)C≡CH | i-Propyl | CH₃ | |
| CH(CH₃)CH₂CH₃ | i-Propyl | C₂H₅ | |
| CH(CH₃)C≡CH | n-Butyl | CH₃ | |
| CH(CH₃)CH₂CH₃ | n-Butyl | C₂H₅ | |
| CH₂C≡CH | C₂H₅ | C₂H₅ | |

V. FORMULATION EXAMPLE

Example 140

For the manufacture of a 50% spray powder, the ingredients listed hereinafter are mixed with one another:

| | |
|---|---|
| Compound in accordance with the invention (active ingredient) | 50 g |
| Silicic acid, hydrated (carrier material, milling aid) | 5 g |
| Sodium lauryl sulphate (wetting agent) | 1 g |
| Sodium lignosulphonate (dispersing agent) | 2 g |
| Kaolin (carrier material) | 42 g |
| | 100 g |

Subsequently, the mixture is finely milled using a pinned disc mill or comparable milling aggregate.

Upon stirring in water the resulting spray powder gives a fine suspension which is suitable as a ready-for-use spray liquor.

We claim:

1. A compound of the formula

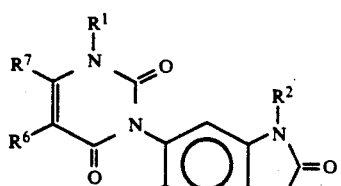

I wherein

R¹ signifies hydrogen, C₁₋₄-alkyl, C₁₋₄-haloalkyl, C₂₋₅-alkenyl or C₃₋₅-alkynyl, R² signifies hydrogen, C₁₋₄-alkyl, C₁₋₄-haloalkyl, C₁₋₄-alkoxy-C₁₋₄-alkyl, C₁₋₄-alkoxy-C₁₋₄-alkoxy-C₁₋₄-alkyl, C₂₋₅-cyanoalkyl, C₂₋₅-carboxyalkyl, C₂₋₅-alkoxycarbonyl-C₁₋₄-alkyl, C₂₋₅-haloalkoxycarbonyl-C₁₋₄-alkyl, C₁₋₄-alkoxy-C₂₋₅-alkoxycarbonyl- $C_{1-4}$-alkyl, $C_{2-5}$-alkoxycarbonyl-$C_{2-5}$-alkoxycarbonyl-$C_{1-4}$-alkyl, $C_{4-7}$-cycloalkyloxycarbonyl-$C_{1-4}$-alkyl, carbamoyl-$C_{1-4}$-alkyl, mono($C_{1-4}$-alkyl)carbamoyl-$C_{1-4}$-alkyl, di($C_{1-4}$-alkyl)carbamoyl-$C_{1-4}$-alkyl, $C_{3\text{ or }4}$-alkenyl, $C_{3\text{ or }4}$-haloalkenyl, cinnamyl, $C_{3\text{ or }4}$-alkynyl or $C_{3\text{ or }4}$-haloalkynyl, $R^5$ signifies hydrogen, fluorine or chlorine, $R^6$ signifies hydrogen, halogen or $C_{1-4}$-alkyl, $R^7$ signifies $C_{1-4}$-alkyl or, where $R^1$ is not $C_{1-4}$-haloalkyl, also $C_{1-4}$-haloalkyl.

and

X signifies oxygen or sulphur, and the enol ethers of those compounds of formula I in which $R^1$ signifies $C_{1-4}$-alkyl, $C_{2-5}$-alkenyl or $C_{3-5}$-alkynyl as well as salts of those compounds of formula I in which $R^1$ signifies hydrogen, $R^2$ signifies hydrogen and/or $R^2$ signifies $C_{2-5}$-carboxyalkyl.

2. A compound according to claim 1, wherein $R^1$ signifies methyl or difluoromethyl.

3. A Compound according to claim 1, wherein $R^2$ signifies $C_{1-4}$-alkyl, $C_{1-4}$-alkoxy-$C_{1-4}$-alkyl, $C_{3\text{ or }4}$-alkenyl or $C_{3\text{ or }4}$-alkynyl.

4. A Compound according to claim 1, wherein $R^5$ signifies hydrogen or fluorine.

5. A Compound according to claim 1, wherein $R^6$ signifies hydrogen, fluorine, chlorine, bromine or methyl.

6. A Compound according to claim 1, wherein $R^7$ signifies methyl, ethyl, trifluoromethyl or pentafluoroethyl.

7. A Compound according to claim 1, wherein X is sulphur.

8. A compound according to claim 1, selected from
6-ethyl-3-[6-fluoro-3-isopropyl-2-oxo-5-benzothiazolinyl]-1-methyl-2,4(1H,3H)-pyrimidinedione,
6-ethyl-3-[3-sec.butyl-6-fluoro-2-oxo-5-benzothiazolinyl]-1-methyl-2,4(1H,3H)-pyrimidinedione,
6-ethyl-3-[6-fluoro-3-(1-methoxyethyl)-2-oxo-5-benzothiazolinyl]-1-methyl-2,4(1H,3H)-pyrimidinedione,
6-ethyl-3-[6-fluoro-3-(1-methoxypropyl)-2-oxo-5-benzothiazolinyl]-1-methyl-2.4(1H,3H)-pyrimidinedione,
6-ethyl-3-[3-allyl-6-fluoro-2-oxo-5-benzothiazolinyl]-1-methyl-2,4(1H,3H)-pyrimidinedione,
6-ethyl-3-[6-fluoro-3-(1-methyl-2-propenyl)-2-oxo-5-benzothiazolinyl]-1-methyl-2,4(1H,3H)-pyrimidinedione,
6-ethyl-3-[6-fluoro-2-oxo-3-(2-propynyl)-5-benzothiazolinyl]-1-methyl-2,4(1H,3H)-pyrimidinedione and
6-ethyl-3-[6-fluoro-3-(1-methyl-2-propynyl)-2-oxo-5-benzothiazolinyl]-1-methyl-2,4(1H,3H)-pyrimidinedione.

9. A compound according to claim 1, wherein $R^6$ signifies $C_{1-4}$ alkyl.

10. A compound according to claim 1, said compound being 3-[6-fluoro-2-oxo-3-isopropyl-5-benzothiazolinyl]-1,6-dimethyl 2,4-(1H,3H)-pyrimidinedione.

11. A weed control composition, which contains an effective amount of at least one compound of the formula

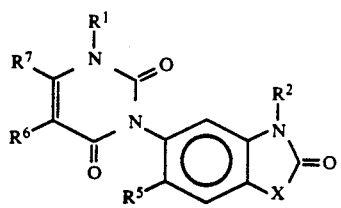

wherein
$R^1$ signifies hydrogen, $C_{1-4}$-alkyl, $C_{1-4}$-haloalkyl, $C_{2-5}$-alkenyl or $C_{3-5}$-alkynyl,
$R^2$ signifies hydrogen, $C_{1-4}$-alkyl, $C_{1-4}$-haloalkyl, $C_{1-4}$-alkoxy-$C_{1-4}$-alkyl, $C_{1-4}$-alkoxy-$C_{1-4}$-alkoxy-$C_{1-4}$-alkyl, $C_{2-5}$-cyanoalkyl, $C_{2-5}$-carboxyalkyl, $C_{2-5}$-alkoxycarbonyl-$C_{1-4}$-alkyl, $C_{2-5}$-haloalkoxycarbonyl-$C_{1-4}$-alkyl, $C_{1-4}$-alkoxy-$C_{2-5}$-alkoxycarbonyl-$C_{1-4}$-alkyl, $C_{2-5}$-alkoxycarbonyl-$C_{2-5}$-alkoxycarbonyl-$C_{1-4}$-alkyl, $C_{4-7}$-cycloalkyloxycarbonyl-$C_{1-4}$-alkyl, carbamoyl-$C_{1-4}$-alkyl, mono($C_{1-4}$-alkyl)carbamoyl-$C_{1-4}$-alkyl, di($C_{1-4}$-alkyl)carbamoyl-$C_{1-4}$-alkyl, $C_{3\text{ or }4}$-alkenyl, $C_{3\text{ or }4}$-haloalkenyl, cinnamyl, $C_{3\text{ or }4}$-alkynyl or $C_{3\text{ or }4}$-haloalkynyl, $R^5$ signifies hydrogen, fluorine or chlorine, $R^6$ signifies hydrogen, halogen or $C_{1-4}$-alkyl, $R^7$ signifies $C_{1-4}$-alkyl or, where $R^1$ is not $C_{1-4}$-haloalkyl, also $C_{1-4}$-haloalkyl, and X signifies oxygen or sulphur, or of an enol ether of such a compound I in which $R^1$ signifies $C_{1-4}$-alkyl, $C_{2-5}$-alkenyl or $C_{3-5}$-alkynyl or of a salt of such a compound I in which $R^1$ signifies hydrogen, $R^2$ signifies hydrogen and/or $R^2$ signifies $C_{2-5}$-carboxyalkyl, as well as formulation adjuvants.

12. A weed control composition according to claim 11, characterized in that it contains an effective amount of at least one compound selected from the group
6-ethyl-3-[6-fluoro-3-isopropyl-2-oxo-5-benzothiazolinyl]-1-methyl-2,4(1H,3H)-pyrimidinedione,
6-ethyl-3-[3-sec.butyl-6-fluoro-2-oxo-5-benzothiazolinyl]-1-methyl-2,4(1H,3H)-pyrimidinedione,
6-ethyl-3-[6-fluoro-3-(1-methoxyethyl)-2-oxo-5-benzothiazolinyl]-1-methyl-2,4(1H,3H)-pyrimidinedione,
6-ethyl-3-[6-fluoro-3-(1-methoxypropyl)-2-oxo-5-benzothiazolinyl]-1-methyl-2,4(1H,3H)-pyrimidinedione,
6-ethyl-3-[3-allyl-6-fluoro-2-oxo-5-benzothiazolinyl]-1-methyl-2,4(1H,3H)-pyrimidinedione,
6-ethyl-3-[6-fluoro-3-(1-methyl-2-propenyl)-2-oxo-5-benzothiazolinyl]-1-methyl-2,4(1H,3H)-pyrimidinedione,
6-ethyl-3-[6-fluoro-2-oxo-3-(2-propynyl)-5-benzothiazolinyl]-1-methyl-2,4(1H,3H)-pyrimidinedione and
6-ethyl-3-[6-fluoro-3-(1-methyl-2-propynyl)-2-oxo-5-benzothiazolinyl]-1-methyl-2,4(1H,3H)-pyrimidinedione as well as formulation adjuvants.

13. A method for the control of weeds, which method comprises treating the locus to be protected against weeds and/or the weeds with an effective amount of a compound in accordance with claim 1 or of a composition in accordance with claim 11.

14. A method for the control of weeds, which method comprises treating the locus to be protected against weeds and/or the weeds with an effective amount of a compound in accordance with claim 3 or of a composition in accordance with claim 12.

* * * * *